(12) United States Patent
Shinbata

(10) Patent No.: US 7,046,836 B2
(45) Date of Patent: May 16, 2006

(54) IMAGE PROCESSING METHOD APPARATUS AND STORAGE MEDIUM FOR RECOGNITION OF IRRADIATION AREA

(75) Inventor: Hiroyuki Shinbata, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/995,153

(22) Filed: Nov. 24, 2004

(65) Prior Publication Data

US 2005/0094860 A1   May 5, 2005

Related U.S. Application Data

(62) Division of application No. 09/287,406, filed on Apr. 6, 1999, now Pat. No. 6,853,740.

(30) Foreign Application Priority Data

| Apr. 7, 1998 | (JP) | ................. | 10-094967 |
| Apr. 7, 1998 | (JP) | ................. | 10-094968 |
| Aug. 28, 1998 | (JP) | ................. | 10-243020 |
| Aug. 28, 1998 | (JP) | ................. | 10-243456 |

(51) Int. Cl.
  *G06K 9/00* (2006.01)
(52) U.S. Cl. ............... 382/132; 382/260; 382/199
(58) Field of Classification Search ............ 382/132, 382/260, 266, 270, 199, 128; 128/922; 378/62, 378/9, 158, 130; 600/481, 9, 407; 250/492.1, 250/363.01
See application file for complete search history.

(56) References Cited

U.S. PATENT DOCUMENTS

| 4,536,797 A | 8/1985 | Maturo et al. |
| 4,710,822 A | 12/1987 | Matsunawa |
| 4,859,850 A | 8/1989 | Funahashi et al. |
| 4,970,393 A | 11/1990 | Funahashi |
| 4,992,663 A * | 2/1991 | Takeo ................. 250/587 |
| 5,046,147 A | 9/1991 | Funahashi et al. |
| 5,081,580 A | 1/1992 | Takeo |
| 5,091,970 A | 2/1992 | Takeo |
| 5,115,476 A * | 5/1992 | Ito ................. 382/199 |
| 5,123,054 A * | 6/1992 | Hara et al. .......... 382/130 |
| 5,151,947 A | 9/1992 | Nagatsuka et al. |
| 5,495,536 A | 2/1996 | Osbourn |
| 5,533,142 A * | 7/1996 | Takeo ................. 382/128 |

(Continued)

FOREIGN PATENT DOCUMENTS

EP   0 750 272   12/1996

(Continued)

OTHER PUBLICATIONS

U.S. Appl. No. 09/154,805, filed Sep. 17, 1998.

*Primary Examiner*—Barry Choobin
(74) *Attorney, Agent, or Firm*—Morgan & Finnegan, LLP

(57) ABSTRACT

An image processing method is intended to extract an irradiation area in an image easily and accurately.

A calculation unit 202 calculates secondary difference values of density values representing respective areas in three areas of a rectangular shape arranged in parallel on an image, determined by a calculation area input unit 200 and a calculation area determination unit 201, between adjacent rectangular areas and the secondary difference values thus calculated are stored in a memory unit 203. Then a judgment unit 204 judges one end point of an irradiation area from the secondary difference values thus stored and an irradiation area determination unit 205 determines the irradiation area, based on a plurality of end points thus judged.

2 Claims, 18 Drawing Sheets

U.S. PATENT DOCUMENTS

| | | | |
|---|---|---|---|
| 5,557,687 A * | 9/1996 | Hara | 382/132 |
| 5,659,402 A | 8/1997 | Fujita et al. | |
| 5,668,889 A * | 9/1997 | Hara | 382/132 |
| 5,732,149 A | 3/1998 | Kido et al. | |
| 5,838,758 A * | 11/1998 | Krug et al. | 378/53 |
| 5,850,465 A * | 12/1998 | Shimura et al. | 382/132 |
| 5,850,836 A * | 12/1998 | Steiger et al. | 600/300 |
| 5,875,225 A * | 2/1999 | Wallschlaeger | 378/15 |
| 5,892,840 A | 4/1999 | Jang et al. | |
| 5,960,102 A * | 9/1999 | Van Eeuwijk et al. | 382/128 |
| 6,002,959 A * | 12/1999 | Steiger et al. | 600/425 |
| 6,061,465 A | 5/2000 | Nakajima | |
| 6,198,837 B1 * | 3/2001 | Sasano et al. | 382/132 |
| 6,243,485 B1 | 6/2001 | Murakami | |
| 6,356,651 B1 * | 3/2002 | Murakami | 382/128 |
| 6,415,049 B1 * | 7/2002 | Yanagita et al. | 382/132 |
| 6,445,771 B1 * | 9/2002 | Buzug et al. | 378/150 |
| 6,600,831 B1 * | 7/2003 | Sasada | 382/132 |
| 6,850,596 B1 * | 2/2005 | Sundermann et al. | 378/147 |
| 6,853,740 B1 * | 2/2005 | Shinbata | 382/132 |
| 6,875,934 B1 * | 4/2005 | Liu et al. | 200/6 A |
| 6,901,158 B1 * | 5/2005 | Shinbata | 382/132 |
| 2002/0113214 A1 * | 8/2002 | Yahiro | 250/492.1 |
| 2002/0146093 A1 * | 10/2002 | Williams | 378/205 |
| 2003/0095698 A1 * | 5/2003 | Kawano | 382/132 |
| 2004/0179646 A1 * | 9/2004 | Li et al. | 378/19 |
| 2004/0197727 A1 * | 10/2004 | Sachdeva et al. | 433/24 |
| 2004/0223591 A1 * | 11/2004 | Sundermann et al. | 378/207 |
| 2005/0069187 A1 * | 3/2005 | Kaji | 382/128 |
| 2005/0094860 A1 * | 5/2005 | Shinbata | 382/132 |
| 2005/0135666 A1 * | 6/2005 | Shinbata | 382/132 |
| 2006/0002302 A1 * | 1/2006 | Bejerano et al. | 370/238 |

FOREIGN PATENT DOCUMENTS

| | | |
|---|---|---|
| JP | 2-1080 | 1/1990 |
| JP | 2-42436 | 2/1990 |
| JP | 2-66683 | 6/1990 |
| JP | 05-007579 | 1/1993 |
| JP | 06-090412 | 3/1994 |
| WO | WO 87 06374 | 10/1987 |

* cited by examiner

IMAGE PROCESSING METHOD APPARATUS AND STORAGE MEDIUM FOR RECOGNITION OF IRRADIATION AREA

This is a divisional of prior application Ser. No. 09/287,406, filed on Apr. 6, 1999, now U.S. Pat. No. 6,853,740, now allowed, which is incorporated herein by reference in its entirety.

BACKGROUND OF THE INVENTION

1. Field of the Invention

The present invention relates to an image processing method, an image processing apparatus, and a storage medium using secondary differences for recognition of an irradiation field.

2. Related Background Art

The recent progress in the digital technology makes it common to convert a radiographic image to a digital image signal, subject this digital image signal to image processing, and display it on a CRT or the like or print it out. In photography of the radiographic image it is common practice to diaphragm the irradiation area so as to radiate the radiation only into a necessary area of a human body on the humane grounds or for the reason of preventing scattering from unnecessary areas so as to prevent lowering of contrast. Normally, a processing parameter is determined from distribution of density values of the image prior to the image processing and the image processing is then carried out based on the parameter thus determined. However, if the irradiation area is not limited, unwanted information, in a sense, outside an area of interest is used for the determination of the image processing parameter, which poses a problem that appropriate image processing is not effected.

It is thus necessary to extract the irradiation area and determine the image processing parameter from information of only the area of interest. As an extraction method of the irradiation area, for example, Japanese Patent Application (Laid-Open) No. 05-007579 describes a method for dividing the image area into small areas and extracting the irradiation area, based on values of variance in the small areas. Further, for example, Japanese Patent Publication No. 6-90412 describes a method for expressing a change of image densities between a predetermined number of pixels near an end portion of the image area by an approximate equation substantially of a linear equation and extracting the irradiation area, based on the difference between assumed image density values according to this approximate equation and actual density values indicated by a sample image signal.

These methods are predicated on the premise that an object area in the photographic image includes the irradiation area (an area actually irradiated), and a process of judging whether the object area is an area including the irradiation area (which will also be referred to as an "area with an irradiation diaphragm") or an area not including the irradiation area (which will also referred to as an "area without the irradiation diaphragm") is carried out as a preliminary operation before execution of these methods.

Methods for judging presence/absence of the irradiation diaphragm include methods for comparing an average, a median, or the like of densities in a central area of the image with an average of densities of the object area and judging that the object area is an area with the irradiation diaphragm, if the average of densities of the object area is not more than a predetermined value, as described in U.S. Pat. No. 5,091,970, for example.

SUMMARY OF THE INVENTION

The method of above Japanese Patent Application (Laid-Open) No. 05-007579 had to obtain the density variance in each small area and thus had the problem of increased computation complexity and computation time. Even within the area of interest, density values vary suddenly, for example, at the edge of the lang field and a change rate of densities could become higher there than at the edge of the irradiation area. Particularly, the variances become high in the area where the lang is in contact with the ribs at the edge of the lang. This caused candidate points for the irradiation area to be extracted from outside the edge of the irradiation area as well and this posed another problem that the judgment became difficult.

In the method of above Japanese Patent Publication No. 6-90412, a foot area outside the irradiation area was assumed for calculation of the linear approximate equation and there arose the problem that the method was invalid if this foot area was not able to be extracted well. Further, it was also assumed that the foot area outside the irradiation area included two areas of a gentle portion and a quickly rising portion and this posed another problem that the method was invalid where the entire foot area was gentle or where there were three or more changes of density gradient.

The present invention has been accomplished in order to solve the problems described above and an object of the invention is, therefore, to extract the irradiation area accurately.

An image processing method of the present invention is an image processing method comprising:

a step of determining a plurality of areas arranged in a predetermined direction on an image and each having a predetermined shape;

a step of calculating a secondary difference value of density values representing the respective areas in the plurality of areas; and a step of judging one end point of an irradiation area from the secondary difference values calculated in the calculating step.

In the conventional image judgment method as described in above U.S. Pat. No. 5,091,970 etc., for example, where the photographic image is one in a state in which the subject overlaps with the edge of the image, the average density value at the end of the image varies depending upon the area of the subject over the edge of the image and upon the transmittance of the radiation. Therefore, the presence/absence of the irradiation diaphragm was sometimes misjudged in the area at the end of the image.

When the radiant dose of the irradiation diaphragm was small, the density difference also became small between the central part of the image and the object area and the presence/absence of the irradiation diaphragm in the object area was misjudged in some cases.

The present invention has been accomplished to eliminate the drawbacks described above and an object of the invention is, therefore, to make it possible to accurately judge whether an image area as a processed object is an area including the irradiation area.

An image processing method of the present invention is an image processing method for extracting an irradiation area in an input image, the image processing method comprising:

a step of detecting an irradiation end, based on a density distribution in each area, for a plurality of areas in a desired direction in the image; and a step of evaluating the result of the detection, based on the result of irradiation ends detected for each of the plurality of areas.

Another image processing method of the present invention is an image processing method for judging whether an object area in an image includes an irradiation area, the method comprising:

a secondary difference value acquisition step of acquiring secondary difference values from one-dimensional image data of the object area;

an irradiation end extraction step of extracting a coordinate of an end point of the irradiation area from the secondary difference values acquired in the secondary difference value acquisition step;

a comparison step of comparing the coordinate extracted in the irradiation end extraction step with a coordinate of an end point of the irradiation area included in the image, the coordinate being obtained preliminarily; and a judgment step of judging whether the object area includes the irradiation area, based on the result of the comparison in the comparison step.

The other objects, arrangements, and effects of the present invention will become more apparent with the description of the embodiments of the present invention which follows.

DETAILED DESCRIPTION OF THE PREFERRED EMBODIMENTS

Embodiment 1

Figure 1:
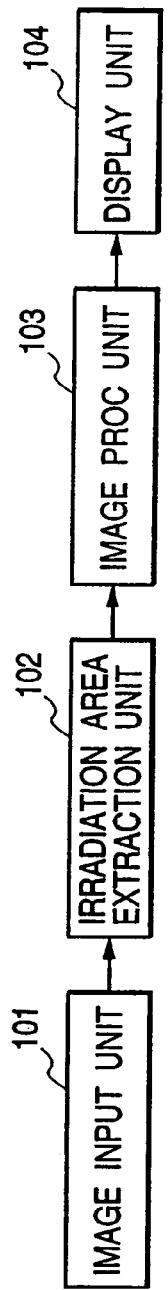
FIG. 1 is a block diagram of an irradiation area extraction device according to Embodiment 1.

FIG. 1 is a block diagram to show the structure of an irradiation area extraction device according to an embodiment of the present invention. In the figure, reference numeral 101 designates an image input unit for accepting input of an image from the outside, 102 an irradiation area extraction unit for extracting an irradiation area irradiated with radiation from the image inputted at the image input unit 101, 103 an image processing unit for performing image processing based on the irradiation area extracted at the irradiation area extraction unit 102, and 104 a display unit for displaying an image subjected to the processing at the image processing unit 103.

Figure 2:
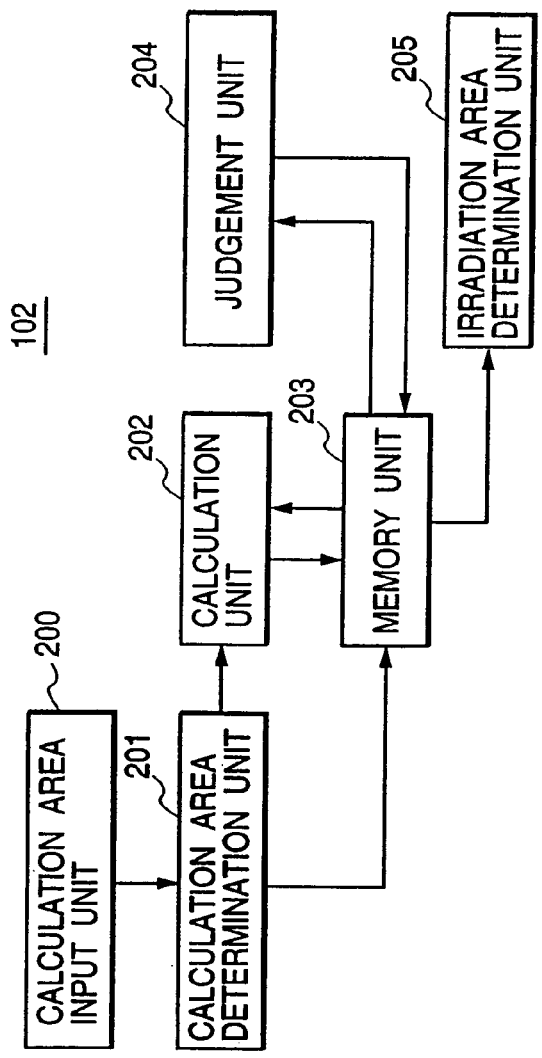
FIG. 2 is a block diagram to show the structure inside an irradiation area extraction unit.

FIG. 2 is a block diagram to show the inside structure of the irradiation area extraction unit 102, in which reference numeral 200 designates a calculation area input unit for accepting input of a direction, a start point, and an end point for determination of calculation areas and 201 a calculation area determination unit for determining, based on the input information at the calculation area input unit 200, areas of calculation carried out by a calculation unit 202 from the input image supplied from the image input unit 101. Numeral 202 denotes a calculation unit for calculating primary difference values and a secondary difference value, described hereinafter, from the calculation areas determined at the calculation area determination unit 201, 204 a judgment unit for judging irradiation area ends, 203 a memory unit for storing the values calculated at the calculation unit 202 and the irradiation area ends judged at the judgment unit 204, and 205 an irradiation area determination unit for determining the irradiation area from the irradiation area ends stored in the memory unit 203 and judged at the judgment unit 204.

Figure 3:
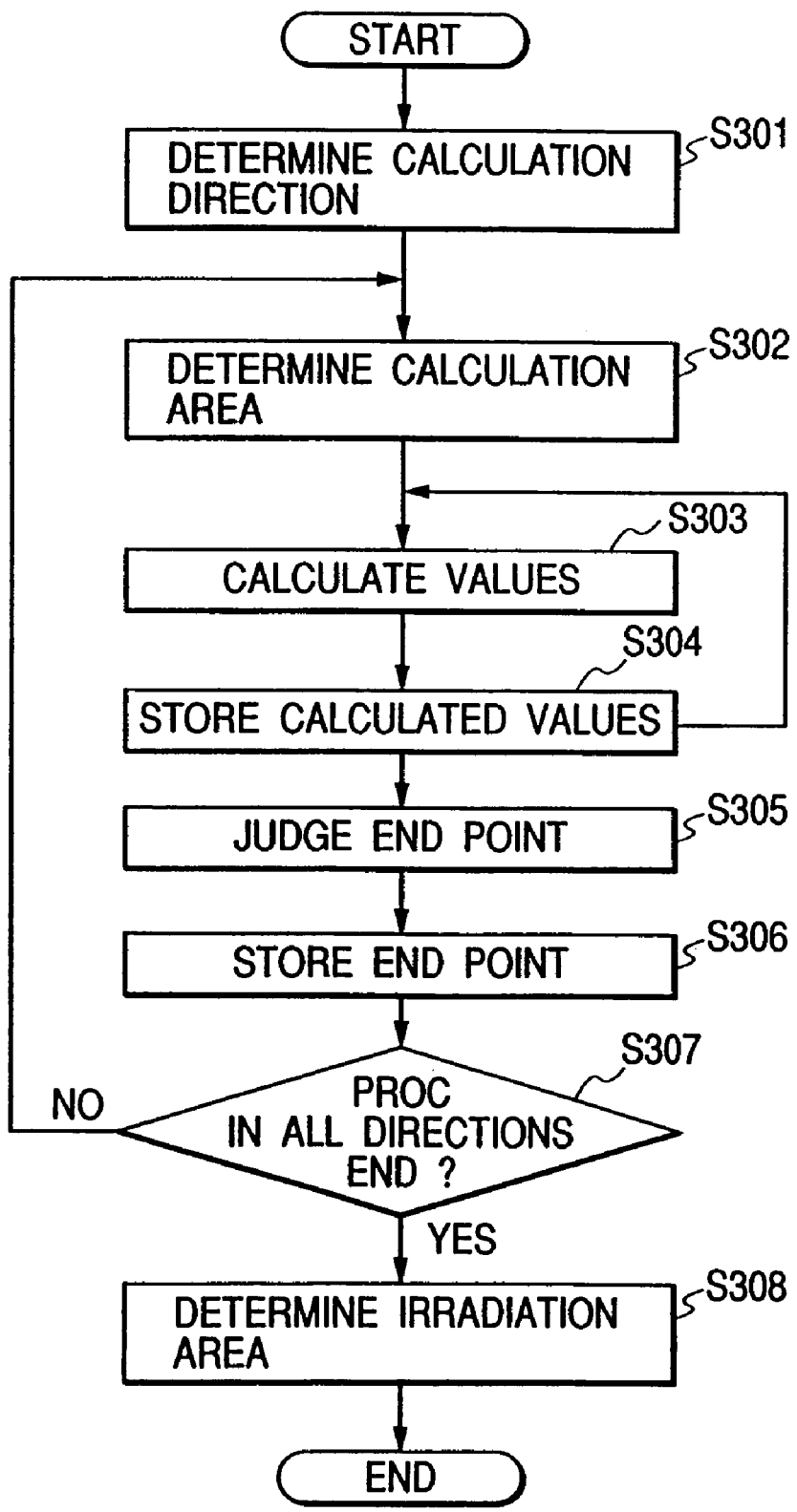
FIG. 3 is a flow chart to show processing procedures in the irradiation area extraction unit.
Figure 4:
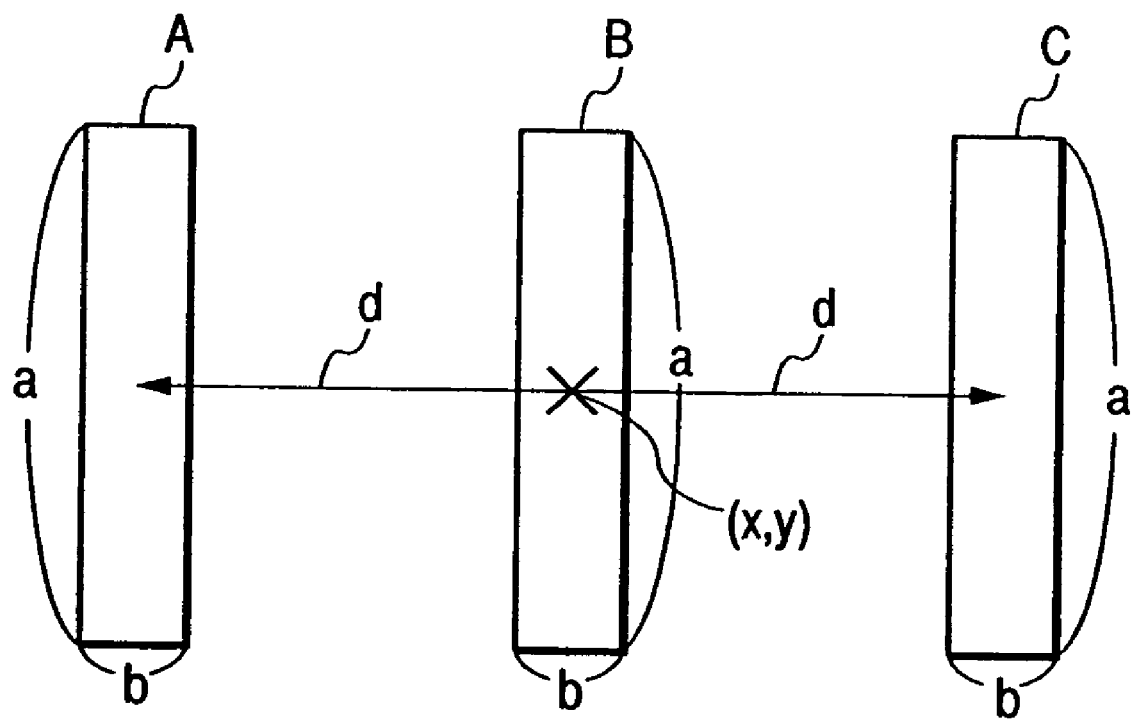
FIG. 4 is a structural diagram to show calculation areas.
Figure 5A:
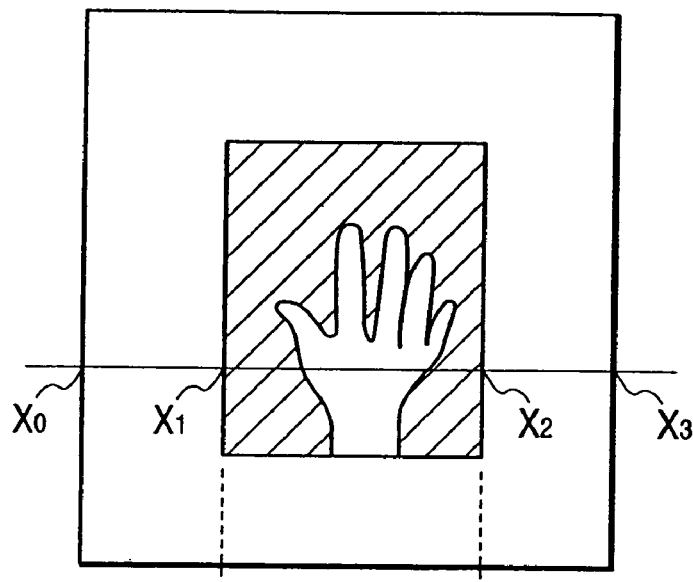
FIG. 5A and FIG. 5B are structural diagrams to show a radiographic image and density values of one line on the radiographic image.
Figure 5B:
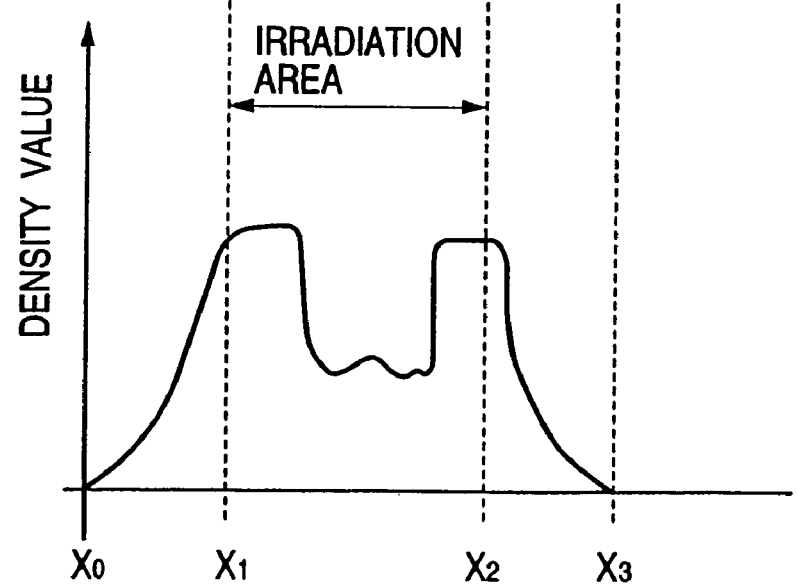
Figure 6A:
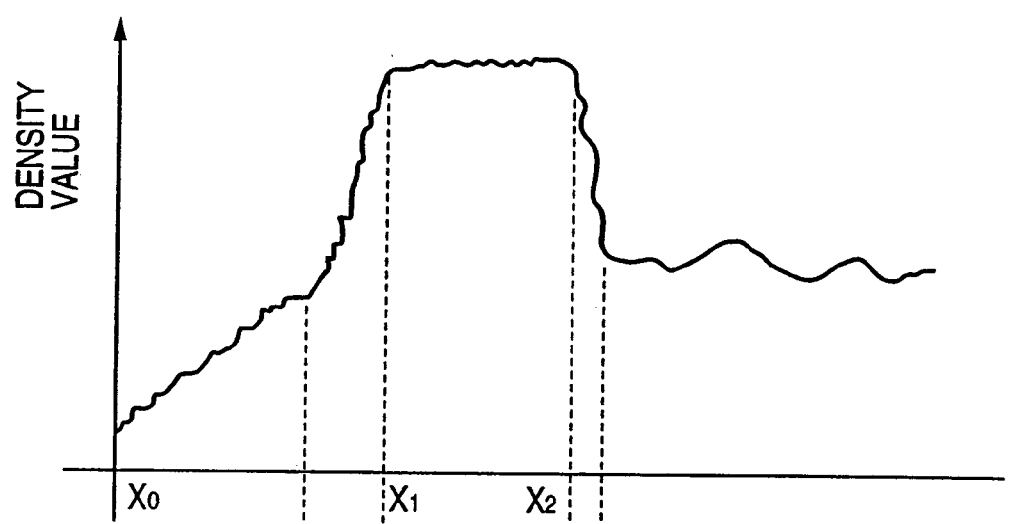
FIG. 6A and FIG. 6B are characteristic diagrams to show density values of one line on FIG. 5A and values of secondary difference on this line.
Figure 6B:
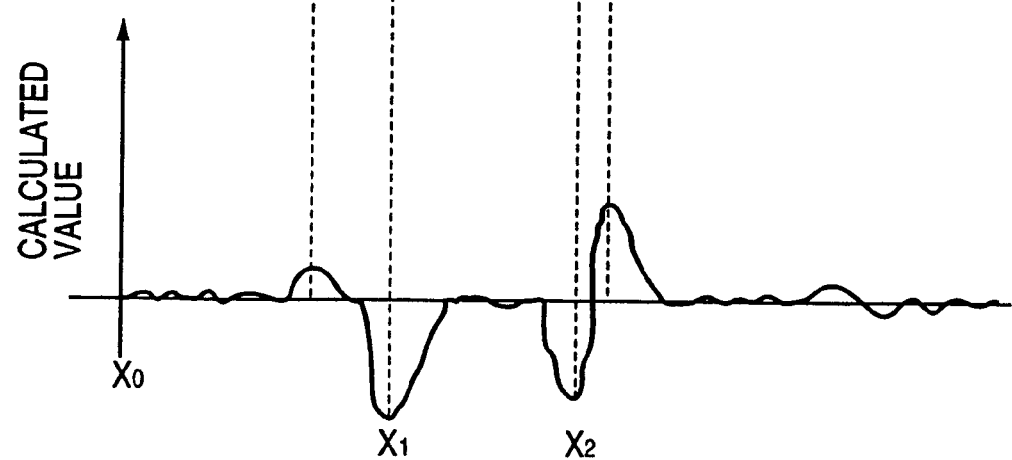

FIG. 3 is a flow chart to show the flow of the processing at the irradiation area extraction unit 102. FIG. 4 is a diagram to show the calculation areas determined at the calculation area determination unit 201. FIG. 5A is a diagram to show a radiographic image and FIG. 5B is a diagram to show density values on line $X_0$ to $X_3$ of FIG. 5A. The abscissa indicates positions on the line $X_0$ to $X_3$ and the ordinate density values on the line. FIG. 6A is an enlarged view of part of FIG. 5B. FIG. 6B is a plot of secondary difference values calculated at the calculation unit 202 against points on the above line between $X_0$ and $X_3$.

The operation will be described below.

In FIG. 1, an image from an external device not illustrated is inputted through the image input unit 101 into the irradiation area extraction unit 102. The irradiation area extraction unit 102 extracts the irradiation area from the input image and delivers the information of the irradiation area to the image processing unit 103. The image processing unit 103 performs the image processing based on the information of the irradiation area extracted at the irradiation area extraction unit 102 and the image through the image processing is displayed on the display unit 104.

The processing at the irradiation area extraction unit 102 of FIG. 2 will be described next according to the flow of FIG. 3. The irradiation area extraction unit 102 receives the input of the calculation direction, the calculation start point, and the calculation end point necessary for the determination of the calculation areas at the calculation area input unit 200 (step S301). It is, however, noted that the input herein is required only for an initial input screen and it does not have to be set for the next input screen and after. Next, the calculation area determination unit 201 determines the calculation areas, based on the information from the calculation area input unit 200. The calculation areas herein are three areas A, B, and C of a rectangular shape arranged in parallel on the image, as illustrated in FIG. 4, and are used as calculation areas for calculation of the secondary difference value at a calculation point indicated by (x,y). These three areas A, B, and C have an equal area which is determined by two parameters of "a" and "b" and the distance between the areas is represented by "d". These parameters "a", "b", "d" are determined experimentally. The calculation area determination unit 201 preliminarily determines the calculation areas for all calculation points and the result, together with information of duplicate calculation areas, is stored in the memory unit 203 (step S302).

Then the calculation unit 202 calculates representatives of density values in the above calculation areas A, B, and C according to a method described hereinafter and further calculates the primary difference values and the secondary difference value. The primary difference values are two values, which are a value "e" resulting from subtraction of the density representative in the area B from the density representative in the area C and a value "f" resulting from subtraction of the density representative in the area A from the density representative in the area B. The secondary difference value is a value resulting from subtraction of the value "f" from the value "e". The primary difference values and secondary difference value calculated in this way are stored in the memory unit 203. From the duplicate information of the calculation areas stored in the memory unit 203, the primary difference values for duplicate calculation areas are obtained from the values stored in the memory unit 203 and the secondary difference value thereof is calculated using them (steps S303 and S304).

Then the judgment unit 204 judges the irradiation area ends from the primary difference values and the secondary difference values stored in the memory unit 203. FIG. 6B shows the secondary difference values calculated at the calculation unit 202. The secondary difference values are negatively large at the points $X_1$ and $X_2$ where the densities vary suddenly, and the aforementioned primary difference values f take positive values in a density increasing direction (when seen from the side of the point $X_0$) but take negative values in a density decreasing direction. From this property the judgment unit 204 judges that a point where the above secondary difference value is minimum and the primary difference values are positive is a candidate for an end point of the irradiation area. If there are plural candidates, the judgment unit determines that a first appearing candidate is an end point of the irradiation area (step S305). Then the irradiation area end point is stored in the memory unit 203 (step S306).

Further, the judgment unit 204 judges whether the processing is completed for all the directions supplied from the calculation area input unit 200 and, if not, the processing is repeated from step S302 (step S307). After the irradiation area end points are determined in all the directions, the irradiation area determination unit 205 determines the irradiation area. Here, a line passing the end point of the irradiation area and being perpendicular to the calculation direction of the secondary difference value (for example, the direction from $X_0$ to $X_3$ in FIGS. 5A and 5B) is calculated for all the end points of the irradiation area and an area surrounded by these lines obtained is determined as an irradiation area (step S308).

The present embodiment presents the effects of less computational complexity and capability of readily extracting the end point of the irradiation area, because the calculation unit 202 is arranged to calculate the representatives of density values in the calculation areas A, B, C and calculate the secondary difference value based on the representative values.

Since the device of the present embodiment has the irradiation area determination unit 205 for determining the irradiation area, the present embodiment has such an effect that the irradiation area can be extracted even if the irradiation area is rectangular, polygonal, or circular. The present embodiment further has such an effect that when the irradiation area is polygonal, an almost circumscribed area can be extracted by selecting directions of lower dimensions than it.

Described below are methods for calculating the representative value in each of the above calculation areas A, B, C. Simple methods for such calculation include a method for calculating an average of all density values (all pixel values) in a calculation area, a method for sorting all the density values in a calculation area according to the density values and using a density value of a pixel at an intermediate position, i.e., a median, and so on. There are also methods for using the limited number of pixels in each calculation area, instead of all the pixels, by sampling or the like according to the necessity and using an average of density values of the limited number of pixels or a median of the limited number of pixels.

Here, when the method for calculating the representative of density values in the calculation area is the method using the average of all the density values in the calculation area, the method has the effect of being resistant to noise. When the representative is determined by the method for sorting all the density values in the calculation area according to the density values and using the density value of the pixel at the intermediate position, the method has the effects of simple calculation and being resistant to noise. Further, when the representative is determined by the method using the average of the limited number of points in the calculation area or the method for sorting the density values of the limited number of points and using the density value at the intermediate position as a representative value, the methods have the effect of capability of further decreasing the computational complexity.

Another approach for determining a representative of each calculation area A, B, C shown in FIG. 4 will be described below. First, let us assume that there are the calculation areas having the vertical height of "a" and the horizontal height of "b", the distance between the areas is represented by "d", and each calculation point is indicated by (x,y), as illustrated in FIG. 4.

In the present embodiment, where the representative value of each area A, B, or C is S(A), S(B), or S(C), respectively, the secondary difference value SS(X) is calculated according to Eq. (1) below.

$$SS(X) = S(A) - 2 \times S(B) + S(C) \quad (1)$$

Next described is a method for calculating the representative value according to this approach where the representative of each area is indicated by S(X) in general. First, a pixel value at each calculation point (x,y) is defined as f(x,y) and values F1(x) are calculated according to Eq. (2) below.

$$F1(x) = \int_0^a f(x, y)dy \quad (2)$$

Here, the integration range is the vertical height "a" of the above rectangular region and for simplicity of the description thereof Eq. (2) is expressed so as to perform the integration in the range of "0" to "a".

Further, values F2(x) are next calculated according to Eq. (3) below.

$$F2(x)=\min\{F1(x+x1)-h(x1)|x1\in K\} \quad (3)$$

Then S(x) is calculated using the values F2(x), according to Eq. (4) below.

$$S(X)=\max\{F2(x-x1)+h(x1)|x1\in K\} \quad (4)$$

Here, h(x) is a function represented by Eq. (5) below and K is a domain of definition thereof.

$$h(x) = 0, \quad -b/4 \leq x \leq b/4 \quad (5)$$
$$= -\infty, \quad \text{otherwise}$$

Then each of the left and right irradiation ends is obtained from a value of x taking minSS(X) in the left half and the right half of the image. The upper and lower ends can also be obtained in a similar fashion.

In other words, the above approach is nothing but an operation in which projection of pixel values is made with respect to a predetermined direction (the vertical direction) of the area, values obtained by the projection are smoothed using a one-dimensional morphology filter, and the secondary difference value is calculated with the distance d.

With this calculation method, the irradiation area can be detected with less errors than in the case of the above methods using the average and median.

The functional blocks 101 to 104, 200 to 205 in FIG. 1 and FIG. 2 may be configured on a hardware basis or may be configured in a microcomputer system comprised of CPU, memory, and so on. When they are configured in the microcomputer system, the above memory comprises the memory medium according to the present invention and this memory medium stores a program for carrying out the processing illustrated in the flow chart of FIG. 3. This memory medium can be selected from semiconductor memories such as ROM, RAM, and the like, optical disks, magneto-optical disks, magnetic media, and so on, or it may be substantiated in the form of either one of a CD-ROM, a floppy disk, a magnetic tape, a non-volatile memory card, and so on.

Since the device according to the present embodiment is arranged to determine the calculation areas comprised of the plural areas of the predetermined shape arranged in the predetermined direction, calculate the secondary difference value of the density values representing the respective areas in the plural areas, and judge one end point of the irradiation area from the secondary difference value thus calculated, the present embodiment presents the effects of capability of decreasing the computational complexity and in turn decreasing the computation time and capability of extracting the end points of the irradiation area with accuracy.

Since the device of the present embodiment is arranged to determine the irradiation area from the plural end points of the irradiation area judged, it can enjoy the effect of capability of extracting the irradiation area even if the irradiation area is rectangular, polygonal, or circular. When the irradiation area is polygonal, the device presents the effect of capability of extracting the almost circumscribed area by selecting directions of lower dimensions than it.

Since the density value representing each area in the plural areas is an average density value in each area, the device can enjoy the effect of capability of extracting the end points of the irradiation area with accuracy even from an image with noise.

Embodiment 2-1

Figure 7:
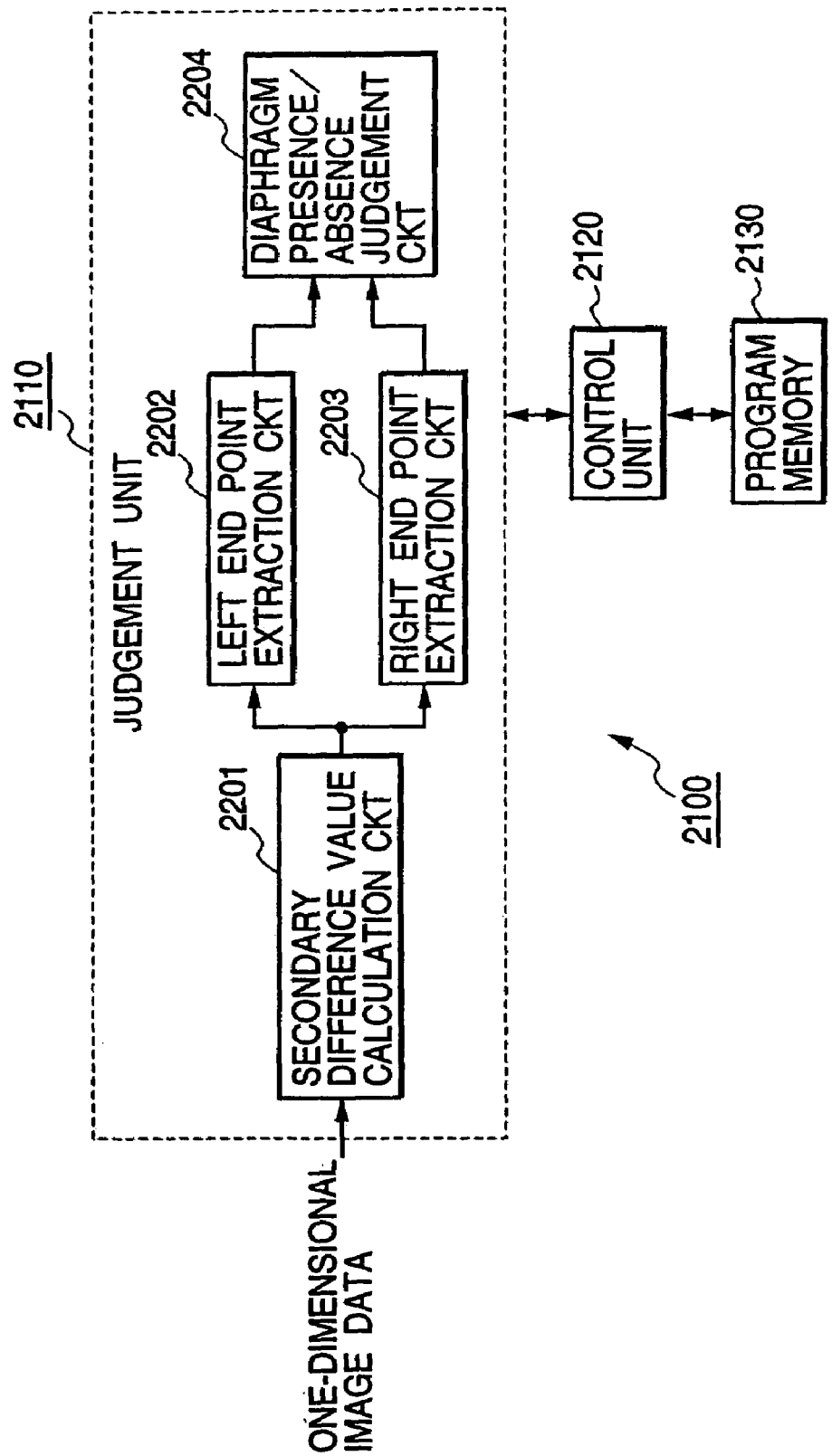
FIG. 7 is a block diagram to show the structure of an image judgment device of Embodiment 2-1.

The present embodiment is carried out, for example, by an image judgment device 2100 illustrated in FIG. 7. This image judgment device 2100 is provided with a judgment unit 2110, a control unit 2120 for carrying out control of the operation of the judgment unit 2110, and a program memory 2130 to which the control unit 2120 makes access, as illustrated in FIG. 7.

The judgment unit 2110 is composed of a secondary difference value calculation circuit 2201 for calculating the secondary difference value from data of an object area in an input image, a left end point extraction circuit 2202 for extracting a left end point of an irradiation area included in the object area, based on the secondary difference value calculated at the secondary difference value calculation circuit 2201, a right end point extraction circuit 2203 for extracting a right end point of the irradiation area included in the object area, based on the secondary difference value calculated at the secondary difference value calculation circuit 2201, and a diaphragm presence/absence judgment circuit 2204 for judging whether the object area is an area with an irradiation diaphragm or an area without an irradiation diaphragm, from the left end point extracted at the left end point extraction circuit 2202 and the right end point extracted at the right end point extraction circuit 2203.

Figure 8:
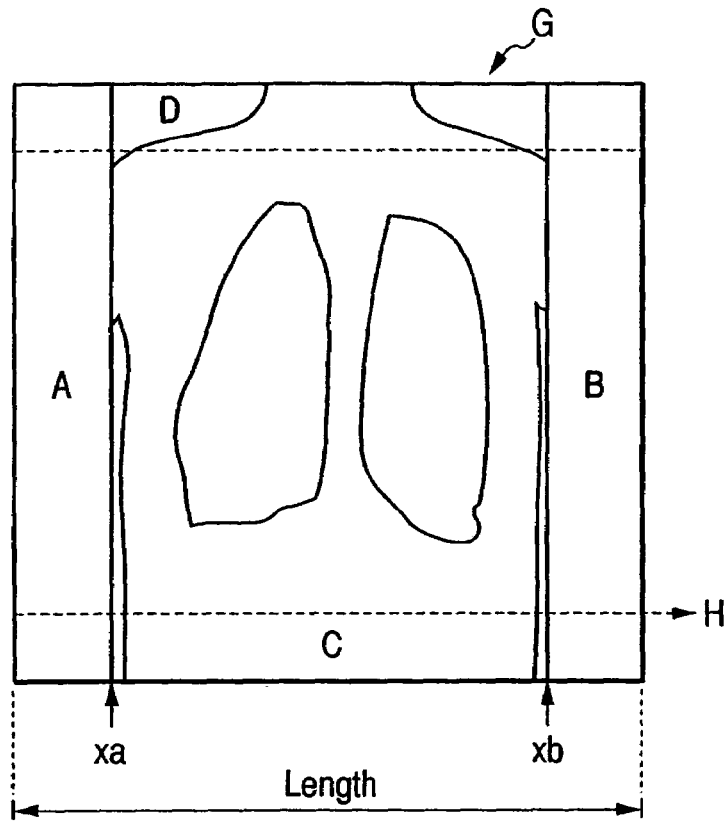
FIG. 8 is a diagram for explaining an example of image data inputted into the above image judgment device.

Here, for example, an image G as illustrated in FIG. 8 is supplied as an input image to the judgment unit 2110. This input image G is a two-dimensional, radiographic, thoracic part image obtained by photographing the thoracic part with the irradiation diaphragm by use of an imaging device with the irradiation diaphragm function.

In above FIG. 8, "$X_a$" and "$X_b$" represent positions of end points (irradiation area ends) of the irradiation area preliminarily obtained with respect to the horizontal axis H, and "A" to "D" are areas at the edges of the image.

These areas A to D are object areas for which whether the irradiation diaphragm is present or absent (i.e., whether the irradiation area is present or absent) is judged. In this example, the areas A and B are areas with the irradiation diaphragm while the areas C and D are areas without the irradiation diaphragm.

Various processing programs for controlling the operation of the judgment unit 2110 are preliminarily stored in the program memory 2130.

Figure 9:
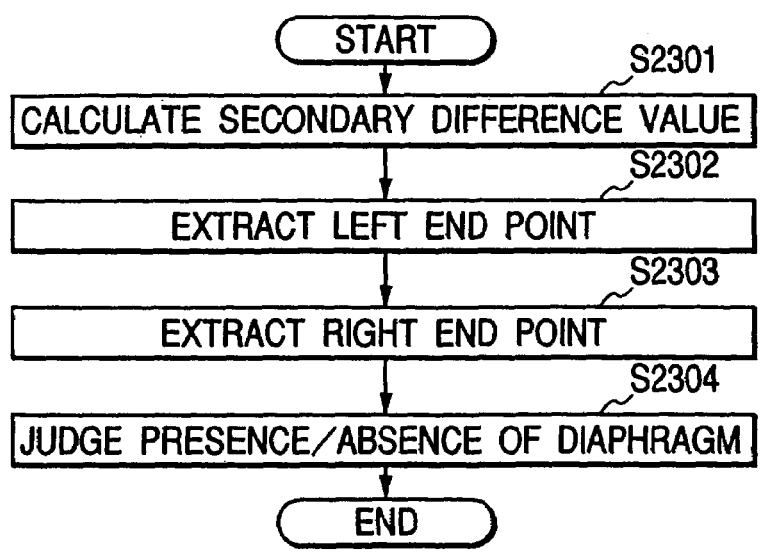
FIG. 9 is a flow chart for explaining a processing program carried out in the above image judgment device.

Specifically, for example, a processing program according to the flow chart as illustrated in FIG. 9 is preliminarily stored in the program memory 2130 and this processing program is read and executed by the control unit 2120, so as to operate the judgment unit 2110 as follows.

First, when the area C is an object area, the secondary difference value calculation circuit 2201 calculates the secondary difference values SS(x) from data of the area C according to Eq. (21) below (step S2301).

$$SS(x)=f(x-d)-2\times f(x)+f(x+d) \quad (21)$$

In this Eq. (21), "f(x)" indicates image data of a one-dimensional line which crosses the area C in the horizontal direction, "x" coordinate values thereof, and "d" a constant indicating a difference distance.

Next, using the secondary difference values SS(x) calculated at the secondary difference value calculation circuit 2201, the left end point extraction circuit 2202 extracts the left end point x1 of the irradiation area included in the area C according to Eq. (22) below (step S2302).

$$SS(x1)=\min\{SS(x)|0\leq x \leq \overline{x}\} \quad (22)$$

$\overline{x}$: coordinates on the horizontal axis between the left and right ends of the object area (coordinates between xa and xb)

On the other hand, using the secondary difference values SS(x) calculated at the secondary difference value calculation circuit 2201, the right end point extraction circuit 2203 extracts the right end point x2 of the irradiation area included in the area C according to Eq. (23) below (step S2303).

$$SS(x2)=\min\{SS(x)|\overline{x}\leq x \leq \text{Length}\} \quad (23)$$

In this Eq. (23), "Length" indicates the length of the area C along the horizontal axis.

Then the diaphragm presence/absence judgment circuit 2204 obtains orders of approximation of the left end point x1 extracted at the left end point extraction circuit 2202 and the right end point x2 extracted at the right end point extraction circuit 2203 with respect to the left and right irradiation end points preliminarily obtained (the positions $X_a$ and $X_b$ of the irradiation ends along the horizontal axis H) and, if the orders of approximation are high, the diaphragm presence/absence judgment circuit 2204 judges that the left end point x1 and the right end point x2 are the left and right end points of the irradiation area (the area irradiated directly), i.e., that the area C is an area without the irradiation diaphragm. On the other hand, if the orders of approximation are low, it is judged that the area C is an area with the irradiation diaphragm (step S2304).

Specifically, using a constant "e" indicating an approximation width, if the below conditions are satisfied the area C is judged as an area without the irradiation diaphragm; otherwise the area C is judged as an area with the irradiation diaphragm.

$$-e \leq x1-X_a \leq e \text{ and}$$

$$-e \leq x2-X_b \leq e$$

When in an object area the irradiation ends are detected similarly to the irradiation ends in the adjacent area, the object area is judged as an area irradiated with radiation as the adjacent area was.

Steps S2301 to S2304 are carried out for each of the other areas A, B, D, in a similar fashion to the area C.

As described above, the present embodiment is arranged to calculate the secondary difference values SS(x) from the data of the object area subjected to the judgment of presence/absence of the radiation diaphragm in the two-dimensional input image G and judge whether the object area is an area with or without the irradiation diaphragm, using the secondary difference values SS(x).

Construction of the device in this structure permits boundary points between the directly irradiated area and the other areas to be extracted with accuracy even from photographic image obtained when a subject with low transmittances of radiation is photographed. Therefore, presence or absence of the irradiation diaphragm can be judged with accuracy for the object areas including the irradiation area. The presence or absence of the irradiation diaphragm can also be judged for an object area in a photographic image in which a portion with low radiation transmittances, such as the abdominal part or the like, overlaps with the edge of the image.

It may also be contemplated that on the occasion of extracting the left end point x1 and the right end point x2 in the object area at the left end point extraction circuit 2202 and at the right end point extraction circuit 2203, another condition for the secondary difference values SS(x) used in the extraction, for example such a condition that the secondary difference values SS(x) are not more than a fixed threshold, is added.

Embodiment 2-2

The present embodiment is arranged to apply, for example, the projection in the object area represented by Eq. (24) below to Eq. (21) in above Embodiment 2-1.

$$f(x) = \int_b^c f(x,y) dy \quad (24)$$

In this Eq. (24), "f(x,y)" represents the image data of the object area in the input image G, and "x" and "y" are coordinates on the horizontal axis and on the vertical axis, respectively. Further, "b" and "c" indicate the object area.

When the projection in the object area represented by above Eq. (24) is used in above Eq. (21) in Embodiment 2-1, it can achieve the effects similar to those in the case where steps S2301 to S2304 described above are carried out in the averaged state of the data of the object area. Namely, misjudgment of presence or absence of the irradiation diaphragm can be prevented from being caused by alteration of coordinates of the object area due to influence of scattered rays, noise, and so on. Therefore, presence/absence of the irradiation diaphragm in the object area can be judged with better accuracy.

Embodiment 2-3

Figure 10:
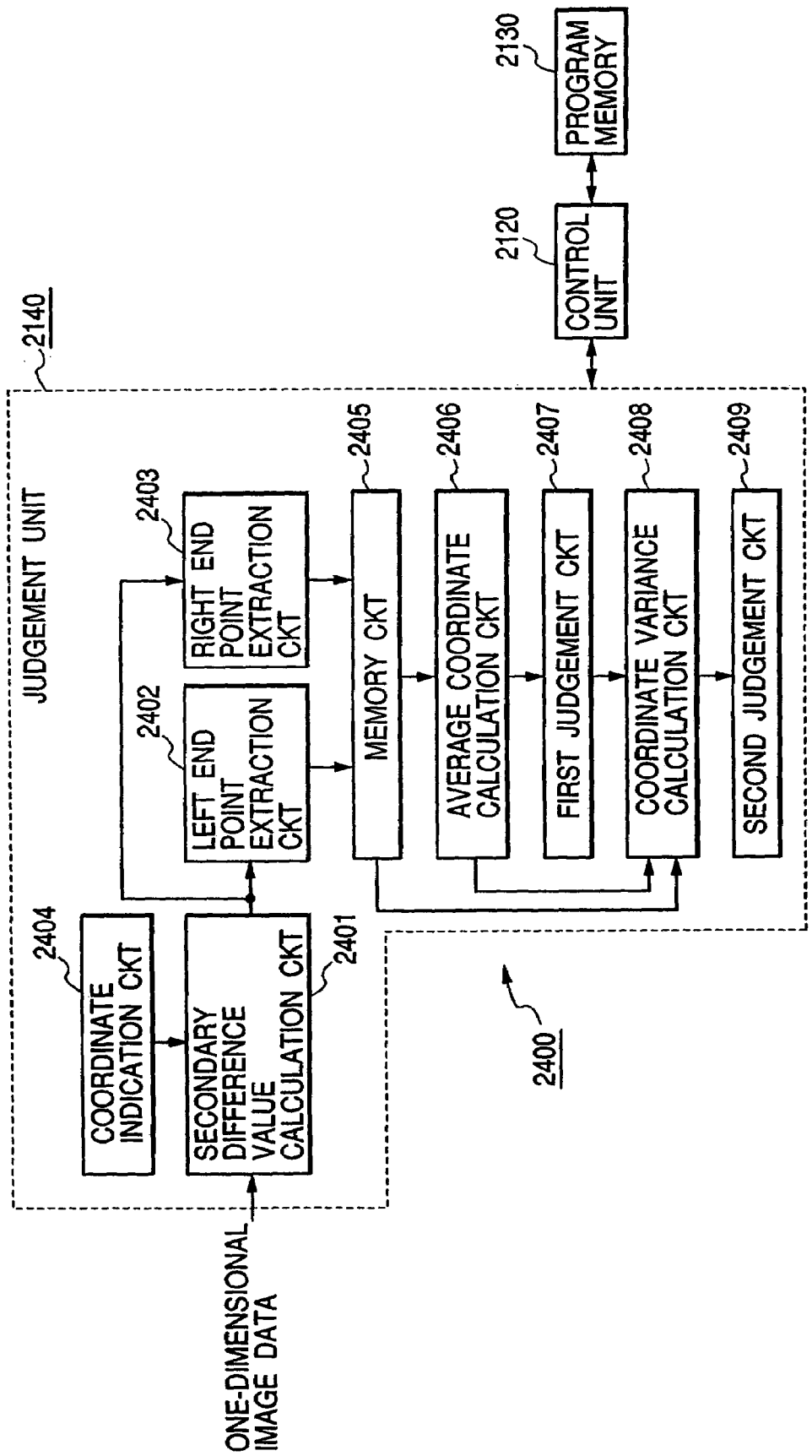
FIG. 10 is a block diagram to show the structure of an image judgment device of Embodiment 2-2.

The present embodiment is applied, for example, to an image judgment device 2400 as illustrated in FIG. 10.

This image judgment device 2400 has the structure similar to that of the image judgment device 2100 in Embodiment 2-1 described above, but is different in the internal structure of the judgment unit 2110 therefrom.

In the image judgment device 2400 of FIG. 10, elements operating similarly to those of the image judgment device 2100 of FIG. 7 are denoted by the same reference symbols and the detailed description thereof is omitted herein. Only the different structure from Embodiment 2-1 will be described in detail herein.

The judgment unit 2140 is composed of, as illustrated in FIG. 10, a coordinate indication circuit 2404, a secondary difference value calculation circuit 2401 for calculating the secondary difference values from data of an object area (either one of the areas A to D in the input image G of FIG. 8 in this example) in the input image according to coordinates indicated by the coordinate indication circuit 2404, a left end point extraction circuit 2402 for extracting a left end point of the irradiation area included in the object area, based on the secondary difference values calculated at the secondary difference value calculation circuit 2401, and a right end point extraction circuit 2403 for extracting a right end point of the irradiation area included in the object area, based on the secondary difference values calculated at the secondary difference value calculation circuit 2401.

The judgment unit 2140 further has a memory circuit 2405 for storing coordinates of a plurality of left and right end points extracted for a plurality of lines by the left end point extraction circuit 2402 and the right end point extraction circuit 2403, an average coordinate calculation circuit 2406 for calculating an average coordinate at each end of the coordinates of the left and right end points stored in the memory circuit 2405, a first judgment circuit 2407 for judging whether the object area is an area with the irradiation diaphragm or an area without the irradiation area, using the averages of the coordinates of the left and right end points calculated at the average coordinate calculation circuit 2406, a coordinate variance calculation circuit 2408 for calculating variances of the coordinates of the left and right end points according to the judgment result of the first judgment circuit 2407, and a second judgment circuit 2409 for again judging whether the object area is an area with the irradiation diaphragm or an area without the irradiation diaphragm, based on the variances calculated at the coordinate variance calculation circuit 2408.

The coordinate indication circuit 2404 is configured to give an indication of a coordinate for calculation of the secondary difference value at the secondary difference value calculation circuit 2401 thereto after the left end point extraction circuit 2402 and the right end point extraction circuit 2403 extract the left and right end points.

Figure 11:
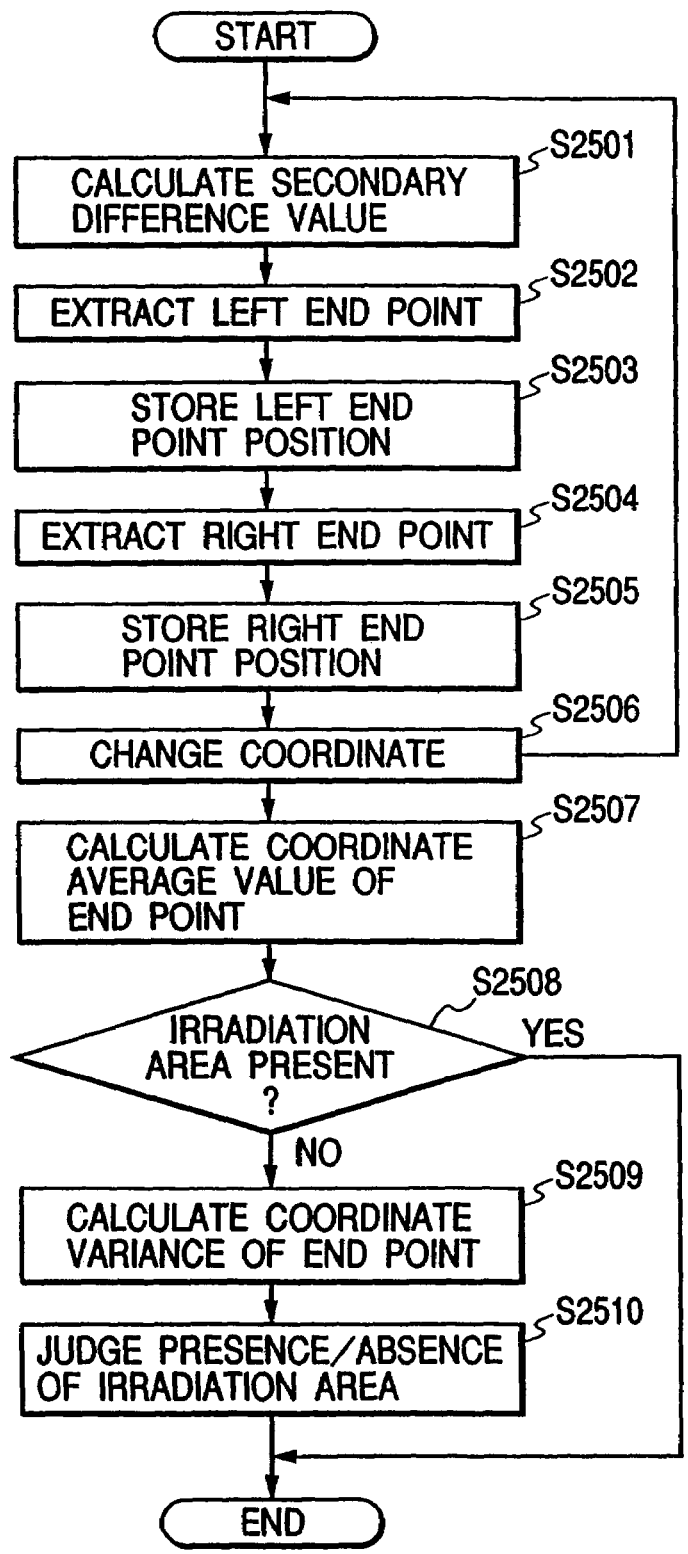
FIG. 11 is a flow chart for explaining a processing program carried out in the above image judgment device.

A processing program, for example, according to the flow chart as illustrated in FIG. 11, for controlling the operation of the judgment unit 2140 is preliminarily stored in the program memory 2130 and this processing program is read and executed by the control unit 2120, whereupon the judgment unit 2140 operates as follows.

First, supposing the area C is an object area, the secondary difference value calculation circuit 2401 calculates the secondary difference values $SSi(x)$ from the data of the area C according to Eq. (25) below for each coordinate i indicated by the coordinate indication circuit 2404 (step S2501).

$$SSi(x) = fi(x-d) - 2 \times fi(x) + fi(x+d) \quad (25)$$

In this Eq. (25), "$fi(x)$" represents image data of a one-dimensional line crossing the area C in the horizontal direction, "x" coordinates thereof, and "i" a coordinate of the horizontal line (a coordinate of the one-dimensional data) indicated by the coordinate indication circuit 2404. Further, "d" is a constant indicating a difference distance.

Using the secondary difference values $SSi(x)$ calculated at the secondary difference value calculation circuit 2401, the left end point extraction circuit 2402 then extracts the left end point xLi according to Eq. (26) below (step S2502).

$$SSi(xLi) = \min\{SSi(x) | 0 \leq x \leq \overline{x}\} \quad (26)$$

$\overline{x}$: coordinates on the horizontal axis between the left and right ends of the object area (coordinates between xa and xb)

Then the memory circuit 2405 stores the left end point xLi extracted at the left end point extraction circuit 2402 (step S2503).

Using the secondary difference values $SSi(x)$ calculated at the secondary difference value calculation circuit 2401, the right end point extraction circuit 2403 also extracts the right end point xRi according to Eq. (27) below (step S2504).

$$SSi(xRi) = \min\{SSi(x) | \overline{x} \leq x \leq \text{Length}\} \quad (27)$$

In this Eq. (27), "Length" indicates the length of the area C along the horizontal axis.

Then the memory circuit 2405 stores the right end point xRi extracted at the right end point extraction circuit 2403 (step S2505).

After completion of the storage of the left end point xLi and the right end point xRi in the memory circuit 2405, the coordinate indication circuit 2404 gives another instruction of a coordinate i of a new horizontal line to the secondary difference value calculation circuit 2401 (step S2506).

According to this indication, the processing from step S2501 is carried out again. This loop processing is executed before the coordinate indication circuit 2404 gives an indication of the end to the secondary difference value calculation circuit 2401.

After steps S2501 to S2506 are carried out repeatedly and the processing is terminated according to the end indication from the coordinate indication circuit 2404, the memory circuit 2405 is in a storage state of the left end points xLi and the right end points xRi corresponding to the coordinates i indicated during the processing by the coordinate indication circuit 2404 to the secondary difference value calculation circuit 2401.

Then the average coordinate calculation circuit 2406 calculates the averages of the left end points xLi and the right end points xRi stored in the memory circuit 2405 (step S2507).

This obtains the average of the left end points xLi (left end point average) XL and the average of the right end points xRi (right end point average) XR.

Next, similar to the irradiation diaphragm judgment circuit 2204 of FIG. 7, the first judgment circuit 2407 compares the left end point average XL and the right end point average XR calculated at the average coordinate calculation circuit 2406 with the left and right irradiation end points preliminarily obtained (the positions $X_a$ and $X_b$ of the irradiation ends on the horizontal axis H), and if the following relations are satisfied it judges that the left and right end points indicated by the left end point average XL and the right end point average XR are the left and right end points of the irradiation area, i.e., that the area C is an area with the irradiation area (or an area without the irradiation diaphragm).

$$-e \leq XL - X_a \leq e \text{ and}$$

$$-e \leq XR - X_b \leq e$$

On the other hand, if either one is not met, the judgment circuit judges that the area C is an area without the irradiation area (or an area with the irradiation diaphragm) (step S2508).

The next steps S2509 and S2510 are carried out only if the first judgment circuit 2407 judges that the area is an area without the irradiation diaphragm.

Namely, the coordinate variance calculation circuit 2408 calculates the variances of the coordinates of the left and right end points, using the left end points xLi and the right end points xRi stored in the memory circuit 2405 and the left end point average XL and the right end point average XR calculated at the average coordinate calculation circuit 2406 (step S2509).

This operation provides the variance VL of the coordinates of the left end points and the variance VR of the coordinates of the right end points.

The second judgment circuit 2409 compares the variances VL and VR of the coordinates of the left and right end points obtained at the coordinate variance calculation circuit 2408 with a predetermined threshold TH. When the following relations are satisfied, the second judgment circuit 2409 judges that the area C is an area with the irradiation area (or an area without the irradiation diaphragm).

VL<TH and

VR<TH

On the other hand, if either one is not met, the second judgment circuit 2409 judges that the area C is an area without the irradiation area (or an area with the irradiation diaphragm) (step S2510).

Steps S2501 to S2510 are also carried out for each of the other areas A, B, D in the similar fashion to the area C.

As described above, the present embodiment is arranged to carry out the detection of the irradiation ends on the plural lines in the object area while the coordinate indication circuit 2404 gives the indications of the coordinates i of one-dimensional data lines crossing the object area in the horizontal direction to the secondary difference value calculation circuit 2401.

Since this structure is arranged to carry out the detection of the irradiation ends on the plural lines in the object area, the present embodiment is more unlikely to be affected by the scattered rays and the noise and can perform the judgment with better accuracy than in the case of the detection of the irradiation ends on a certain line.

Since the variances of the irradiation ends are also used for the judgment of presence/absence of the irradiation diaphragm by provision of the second judgment circuit 2409, for example, when the image end portions are exposed to radiation because of the influence of the scattered rays, so as to result in making the irradiation ends extracted in the image end portions coincident with the irradiation ends preliminarily obtained, the degree of spread of the scattered rays can be quantified and thus misjudgment of presence/absence of the irradiation diaphragm can be prevented for sure.

Embodiment 2-4

The present embodiment is arranged to calculate the secondary difference values SS(x) according to above Eq. (21) and to extract the left end point x1 of the irradiation area included in the object area, using the secondary difference values SS(x), for example, similar to Embodiment 2-1 described above. At this time the present embodiment also uses the sign of the primary difference value S(x1) given by Eq. (28) below.

$$S(x1)=f(x1)-f(x1-d) \quad (28)$$

Specifically, for example, if the sign of the primary difference value S(x1) is "negative" and if above Eq. (22) is satisfied, the left end point x1 is regarded as a left end point of the irradiation area.

For extracting the right end point x2 of the irradiation area included in the object area, the present embodiment also uses the sign of the primary difference value S(x2) given by Eq. (29) below.

$$S(x2)=f(x2+d)-f(x2) \quad (29)$$

For example, if the sign of the primary difference value S(x2) is "negative" and if above Eq. (23) is satisfied, the right end point x2 is regarded as a right end point of the irradiation area.

Using the left end point x1 and the right end point x2 obtained in this way, the judgment of presence/absence of the irradiation diaphragm in the object area is carried out in the similar fashion to that in Embodiment 2-1 described above.

When the conditions of the signs of the primary difference values are also added to the detection of the irradiation ends of the object area, presence/absence of the irradiation diaphragm in the object area can be judged with consideration to the inclination of image data outside the irradiation area due to the scattered rays. This permits the presence/absence of the irradiation diaphragm in the object area to be judged without misjudgment and with better accuracy even if there is a portion or the like where densities change quickly in the object area.

Embodiment 2-5

The present embodiment is arranged first to calculate the secondary difference values from the data of the object area, for example similar to Embodiment 2-1, but at this time, the present embodiment is arranged to calculate the secondary difference values from data obtained after the data of the object area is filtered.

Specifically, for example, the image data of a one-dimensional line of an object area is represented by "f(x)", the data is subjected to a filtering process according to Eqs. (30) and (31) below, and the secondary difference values are calculated from the values F2 obtained as a result.

$$F1(x)=\min\{f(x+x1)-h(x1)|-d \leq x1 \leq d\} \quad (30)$$

$$F2(x)=\max\{F1(x-x1)+h(x1)|-d \leq x1 \leq d\} \quad (31)$$

$$h(x) \begin{cases} =0: & -d \leq x \leq d \\ =-\infty: & \text{otherwise} \end{cases}$$

When Embodiment 2-1 is modified so as to calculate the second difference values after the data of the object area is smoothed by the filtering process as described above, the presence/absence of the irradiation diaphragm in the object area can be judged with better accuracy without influence of the noise, particularly, without influence of the noise on the line.

Embodiment 3-1

Figure 12:
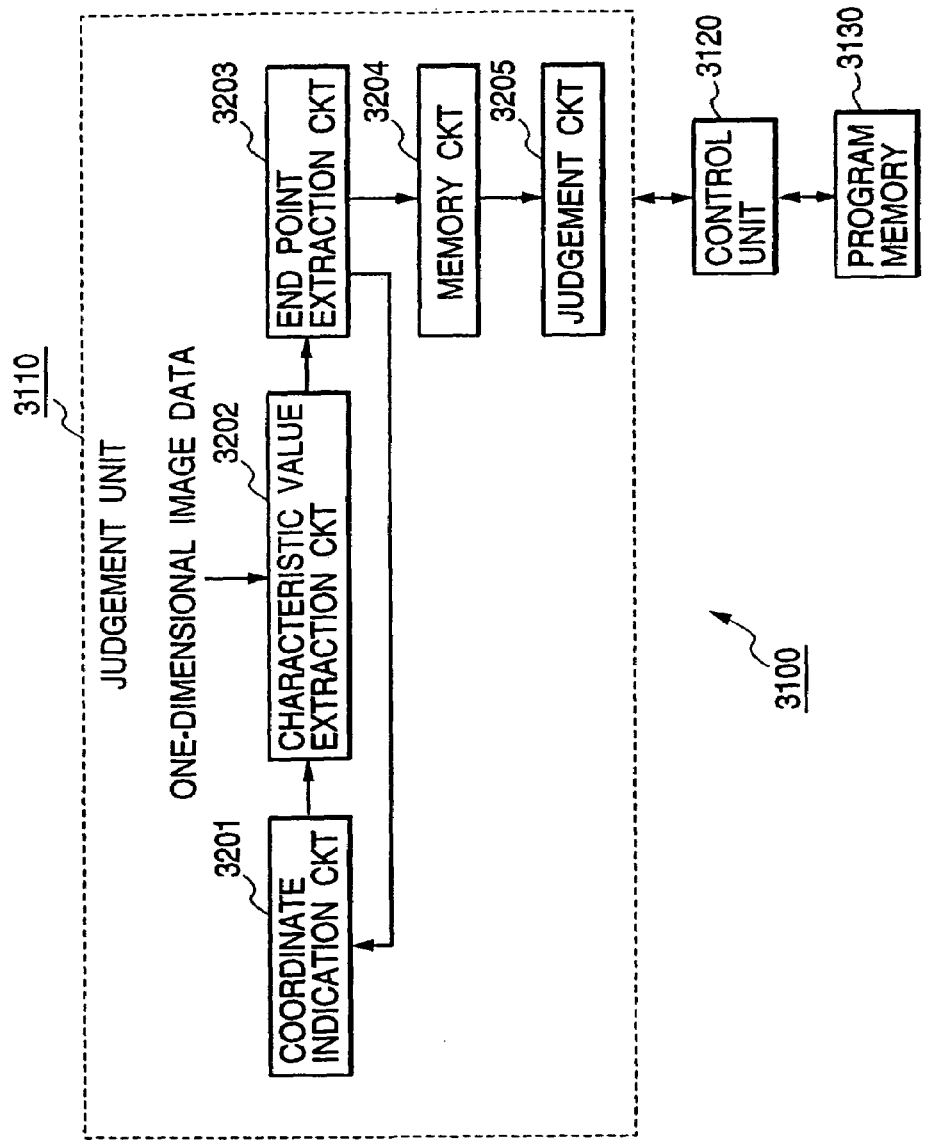
FIG. 12 is a block diagram to show the structure of an image judgment device of Embodiment 3-1.

The present embodiment is carried out, for example, by an image judgment device 3100 as illustrated in FIG. 12.

This image judgment device 3100 is composed of a judgment unit 3110, a control unit 3120 for controlling the operation of the judgment unit 3110, and a program memory 3130 to which the control unit 3120 makes access, as illustrated in FIG. 12.

The judgment unit 3110 is composed of a coordinate indication circuit 3201, a characteristic value extraction circuit 3202 for extracting a characteristic value from data of an object area in an input image according to a coordinate indicated by the coordinate indication circuit 3201, an end point extraction circuit 3203 for extracting a coordinate of an end point of the irradiation area included in the object area, based on the characteristic value extracted at the characteristic value extraction circuit 3202, a memory circuit 3204 for storing coordinates of end points extracted at the end point extraction circuit 3203, and a judgment circuit 3205 for judging whether the object area is an area with the irradiation diaphragm or an area without the irradiation diaphragm, from the coordinates of the end points stored in the memory circuit 3204.

Figure 13:
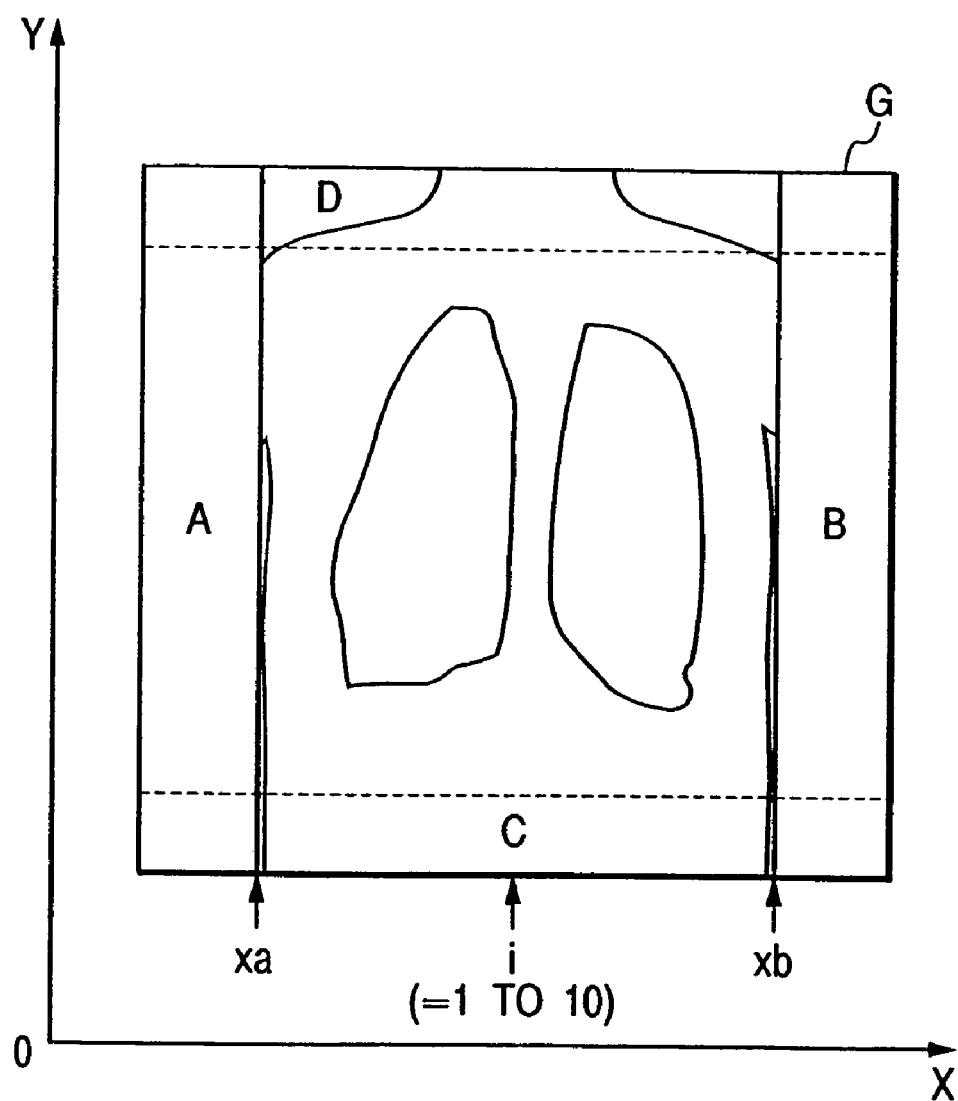
FIG. 13 is a diagram for explaining an example of image data inputted into the above image judgment device.

Here, for example, an image G illustrated in FIG. 13 is supplied as an input image to the judgment unit 3110. This input image G is a two-dimensional, radiographic, thoracic part image obtained by photographing the thoracic part with the irradiation diaphragm by use of an imaging device with the irradiation diaphragm function.

In above FIG. 13, "$X_a$" and "$X_b$" represent positions of irradiation area ends on the horizontal axis X. "A" to "D" are areas at the edges of the image part. In this example, the areas A and B out of these "A" to "D" are areas with the irradiation diaphragm while the other areas C and D are areas without the irradiation diaphragm.

Various processing programs for controlling the operation of the judgment unit 3110 are preliminarily stored in the program memory 3130.

Figure 14:
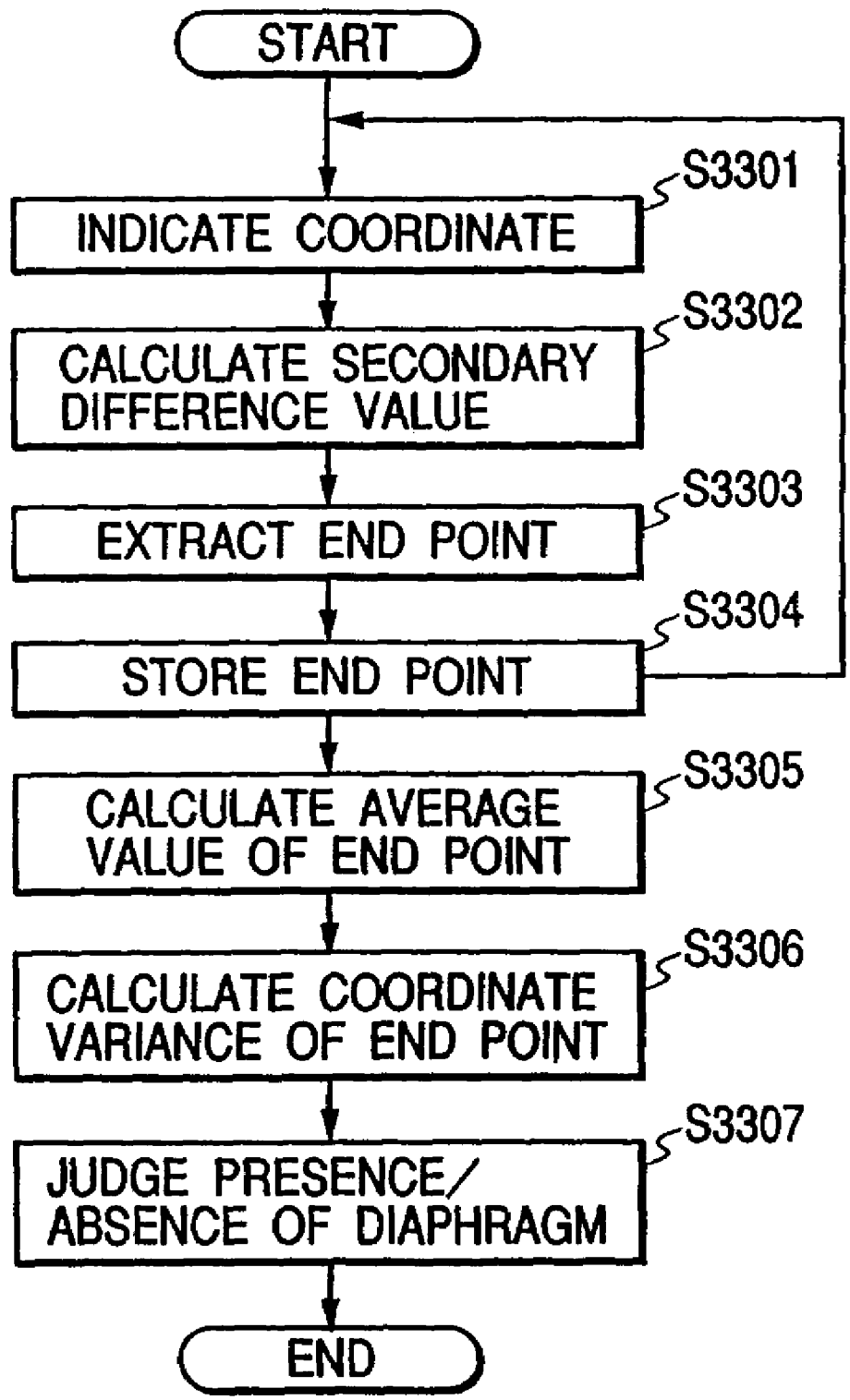
FIG. 14 is a flow chart for explaining a processing program carried out in the above image judgment device.

Specifically, for example, a processing program according to the flow chart as illustrated in FIG. 14 is preliminarily stored in the program memory 3130 and this processing program is read and executed by the control unit 3120 to operate the judgment unit 3110 as follows.

Described below is a process of judging whether the irradiation diaphragm is present or absent at the lower edge.

First, the coordinate indication circuit 3201 gives indications of plural coordinates on the X-axis between $X_a$ and $X_b$ in the input image G of above FIG. 13 to the characteristic value extraction circuit 3202 (step S3301).

Specifically, the coordinate indication circuit 3201 successively indicates, for example, coordinates i (=1 to 10) on the X-axis, which are ten points distributed at equal intervals between $X_a$ and $X_b$.

According to each coordinate i indicated by the coordinate indication circuit 3201, the characteristic value extraction circuit 3202 then calculates a characteristic value of one-dimensional image data corresponding to the coordinate i, for example, the secondary difference values SSi(y) according to Eq. (41) below (step S3302).

$$SSi(y)=fi(y-d)-2\times fi(y)+fi(y+d) \quad (41)$$

In this Eq. (41), "fi(y)" indicates image data of a one-dimensional line crossing the object area in the vertical direction, "y" coordinates thereof, and "d" a constant indicating a difference distance.

Using the secondary difference values SSi(y) obtained at the characteristic value extraction circuit 3202, the end point extraction circuit 3203 then extracts a coordinate yi of an end point (an irradiation end point) of the irradiation area included in the object area according to Eq. (42) below (step S3303).

$$SS(yi)=\min\{SSi(y)|0\leq y\leq \text{Length}\} \quad (42)$$

In this Eq. (42), "Length" represents the length of the input image G along the vertical axis (the direction of the Y-axis).

Then the memory circuit 3204 stores the coordinate yi of the irradiation end point obtained at the end point extraction circuit 3203 (step S3304).

The above processing of steps S3301 to S3304 is carried out repeatedly before the coordinate i indicated by the coordinate indication circuit 3201 reaches "10". This results in storing the coordinates y1, y2, y3, . . . , y10 of the irradiation end points corresponding to the coordinates i=1, 2, 3, . . . , 10 indicated by the coordinate indication circuit 3201, in the memory circuit 3204.

After completion of the processing of steps S3301 to S3304 up to the coordinate i=10, the judgment circuit 3205 then calculates an average of the coordinates y1, y2, y3, . . . , y10 stored in the memory circuit 3204 (step S3305) and calculates a variance Bv of the irradiation end points (step S3306).

Then the judgment circuit 3205 judges that the object area is an area without the irradiation diaphragm, if the variance Bv is not less than a predetermined threshold TH; otherwise, it is judged that the object area is an area with the irradiation diaphragm (step S3307).

The threshold TH is a constant which is determined experimentally.

As described above, the present embodiment is arranged to carry out the extraction of irradiation ends of plural column lines in the object area for which presence/absence of the irradiation diaphragm is judged and judge the presence/absence of the irradiation diaphragm of the object area according to the variance of the irradiation ends. If there is an irradiation area in the object area the coordinates of the irradiation end points of the plural column lines will be aligned approximately on one horizontal axis and the variance thereof will be thus small. If there is no irradiation area in the object area the coordinates of the irradiation end points of the plural column lines will be distributed and the variance will be thus large.

Therefore, the presence/absence of the irradiation diaphragm in the object area can be determined with accuracy because of the structure using the variance.

Since the device is constructed to use the secondary difference value in order to extract the irradiation end, boundary points can be extracted with accuracy between an area irradiated directly and the other areas even in a photographic image obtained by photographing a subject with low transmittances of radiation. Therefore, the device of the present embodiment can judge the presence/absence of the irradiation diaphragm in the object area including the irradiation area with accuracy. In addition, the presence/absence of the irradiation diaphragm in the object area can be judged with accuracy even in a photographic image in which a portion with low radiation transmittances such as the abdominal part or the like overlaps with an end portion of the image.

Although the present embodiment is arranged to use the secondary difference value in order to make a judgment of the irradiation diaphragm, the apparatus of the present invention does not always have to be limited to this; for example, where change of density is quick at an irradiation end, the apparatus may also be arranged to use the primary difference values or higher-order difference values. In this case, the primary difference values or the higher-order difference values are obtained from the object area and a first appearing point of a value not less than a predetermined threshold is regarded as a candidate for an irradiation end.

Although the present embodiment is arranged to use the variance in order to make a judgment of the irradiation diaphragm, the apparatus of the present invention does not always have to be limited to this; for example, the apparatus may also be arranged to use another index that can indicate discrete degrees of frequency, such as standard deviation.

Embodiment 3-2

The present embodiment is arranged to apply the projection of a constant width in an object area according to Eq. (43) below to Eq. (41) in Embodiment 3-1 described above.

$$fi(y) = \int_{xi-1}^{xi} f(x, y)dx \tag{43}$$

In this Eq. (43), "fi(y)" represents image data of a one-dimensional line in the object area in above Eq. (41), and "Xi" and "Xi−1" represent coordinates indicated by the coordinate indication circuit 3201.

When Embodiment 3-1 is modified so as to apply the projection in the object area represented by above Eq. (43) to above Eq. (41) as described above, the modification can enjoy the same effects as in the case where aforementioned steps S3301 to S3307 are carried out in an averaged state of the data of the object area. Namely, this structure can prevent misjudgment about the presence/absence of the irradiation diaphragm from being caused by change of coordinates of the object area due to influence of the scattered rays, the noise, and so on. The presence/absence of the irradiation diaphragm in the object area can be judged with better accuracy accordingly.

Embodiment 3-3

The present embodiment is arranged to calculate the secondary difference values SSi(y) according to above Eq. (41) and extract the irradiation end of the object area using the secondary difference values SSi(y), for example, as Embodiment 3-1 described above was. At this time, the present embodiment also uses the sign of the primary difference value Si(y) expressed by Eq. (44) below.

$$Si(y)=fi(y)-fi(y-d) \tag{44}$$

Specifically, for example, if the sign of the primary difference value Si(y) is "negative" and if above Eq. (42) is satisfied, the point "y" is regarded as an irradiation end.

Using the irradiation ends obtained in this way, whether the irradiation diaphragm is present or absent in the object area is judged in the similar fashion to aforementioned Embodiment 3-1.

When Embodiment 3-1 is modified to use the sign of the primary difference value as well on the occasion of detecting the irradiation end in the object area, the presence/absence of the irradiation diaphragm in the object area can be judged, also taking the inclination of image data outside the irradiation area due to the scattered rays into consideration. Therefore, whether the irradiation diaphragm is present or absent in the object area can be judged with better accuracy without misjudgment, even if there is a quickly changing portion of density or the like within the object area.

Embodiment 3-4

The present embodiment is arranged first to calculate the secondary difference values from the data of the object area, similar to Embodiment 3-1; but at this time, the data of the object area is subjected to a filtering process and the secondary difference values are calculated from the data after the filtering process.

Specifically, for example, where the image data of a one-dimensional line of the object area is "f(x)", it is subjected to the filtering process according to Eq. (45) and Eq. (46) below and the secondary difference values are calculated from values F2 obtained as a result.

$$F1i(y)=\min\{fi(y+y1)-h(y1)|-d \leq y1 \leq d\} \tag{45}$$

$$F2i(y)=\max\{F1i(y-y1)+h(y1)|-d \leq y1 \leq d\} \tag{46}$$

$$h(x) = \begin{cases} 0: & -d \leq x \leq d \\ -\infty: & \text{otherwise} \end{cases}$$

When Embodiment 3-1 is modified so as to calculate the secondary difference values after the data of the object area is smoothed by the filtering process as described above, whether the irradiation diaphragm is present or absent in the object area can be judged with better accuracy without being affected by the noise, particularly, without being affected by the noise on the line.

Embodiment 4-1

Figure 15:
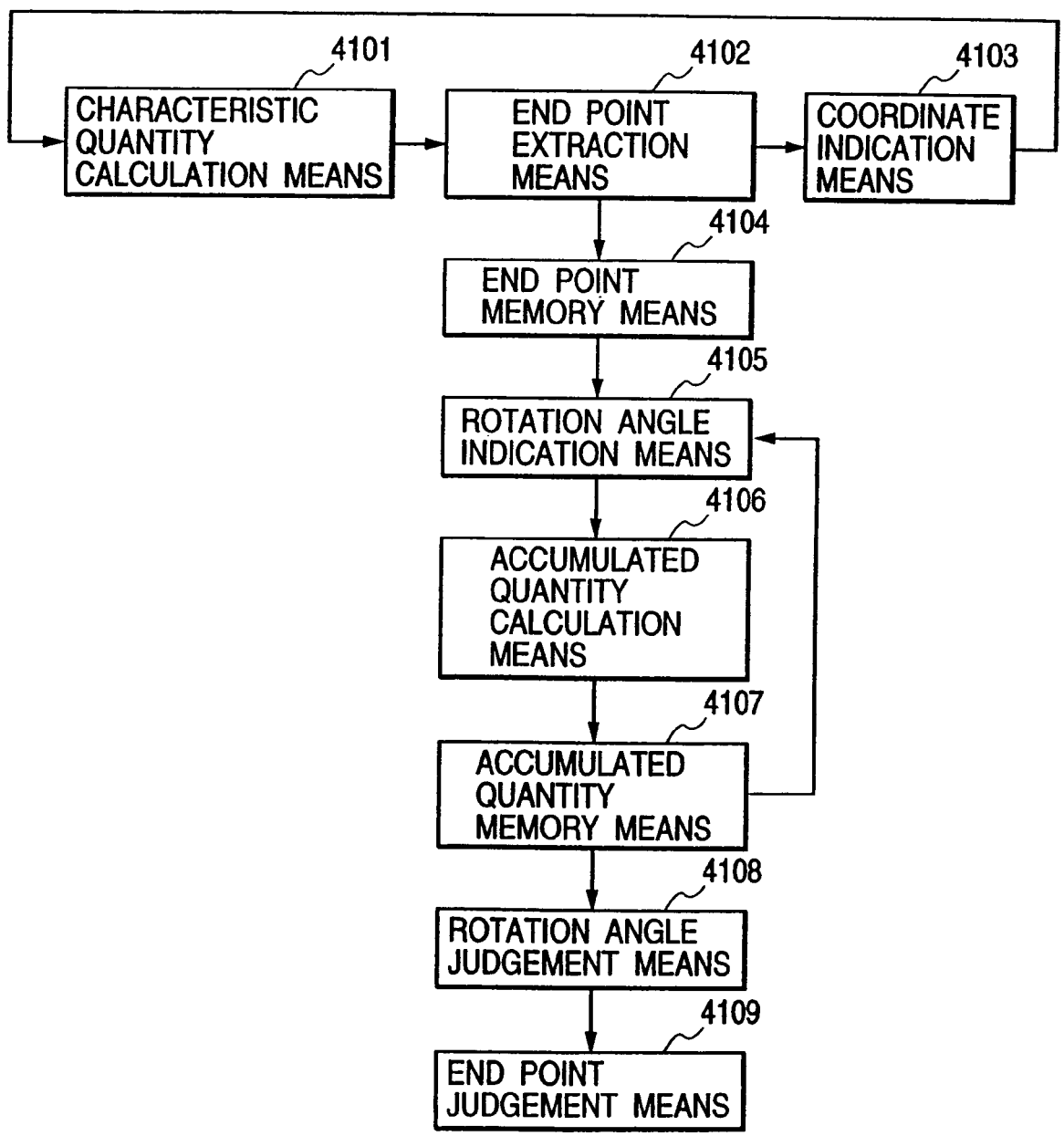
FIG. 15 is a block diagram to show the structure of an angle extraction device and an area extraction device in Embodiment 4-1.

FIG. 15 is a block diagram to show the structure of an angle extraction device and an area extraction device of two-dimensional image data according to Embodiment 4-1. In FIG. 15, reference numeral 4101 designates a characteristic quantity calculation means for calculating a characteristic quantity from data of a one-dimensional line at a coordinate indicated by a coordinate indication means 4103, 4102 an end point extraction means for extracting an area end portion from the characteristic quantity calculated at the characteristic quantity calculation means 4101, 4103 a coordinate indication means for indicating a coordinate of image data to be calculated by the characteristic quantity calculation means 4101, 4104 an end point memory means for storing a coordinate of an end point extracted at the end point extraction means 4102, and 4105 a rotation angle indication means for indicating a rotation angle of a rotation axis onto which coordinates of end points stored in the end point memory means 4104 are projected.

Reference numeral 4106 denotes an accumulated quantity calculation means for calculating an accumulated quantity of the coordinates of the end points projected onto the aforementioned rotation axis and stored in the end point memory means 4104, 4107 an accumulated quantity memory means for storing the accumulated quantity calculated at the accumulated quantity calculation means 4106, 4108 a rotation angle judgment means for judging a rotation angle from the accumulated quantity stored in the accumulated quantity memory means 4107, and 4109 an end point judgment means for extracting an area end from the angle judged at the rotation angle judgment means 4108 and the accumulated quantity stored in the accumulated quantity memory means 4107.

Figure 16:
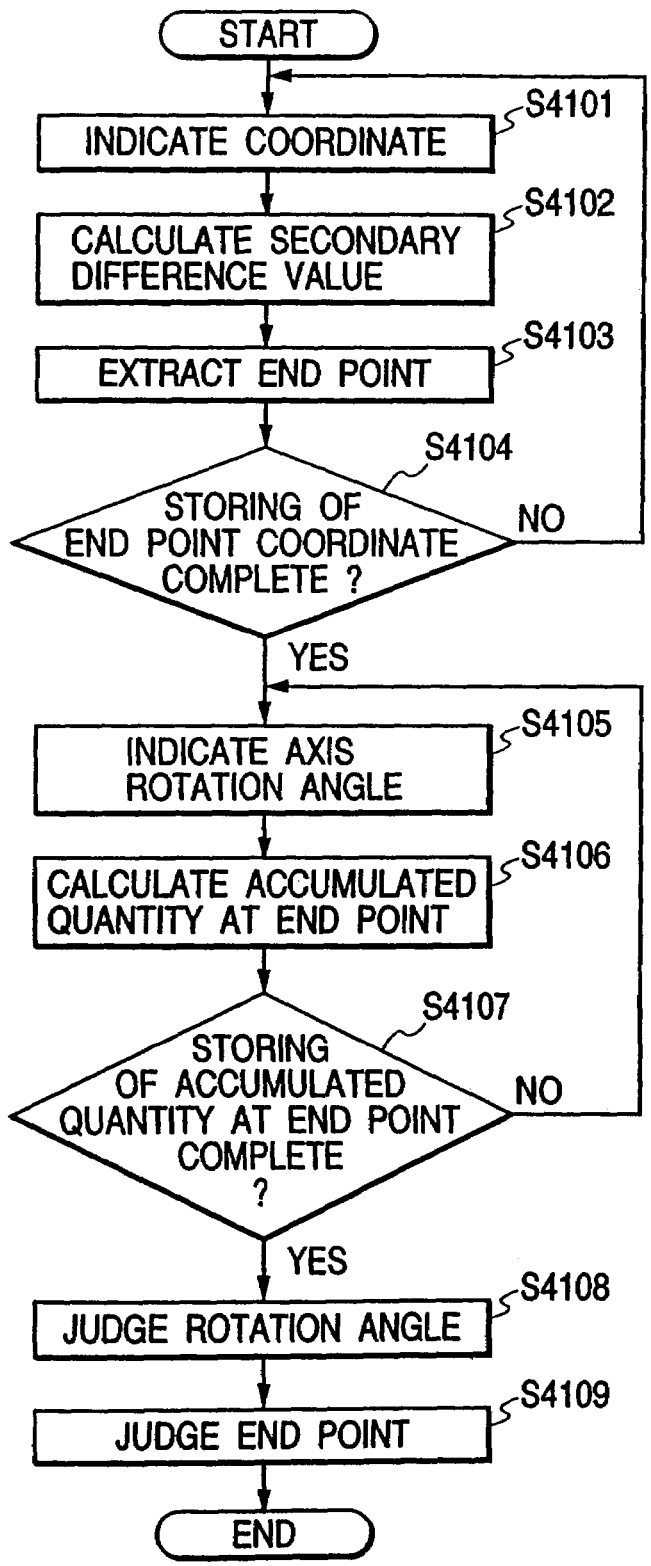
FIG. 16 is a flow chart of a processing procedure sequence in the angle extraction device and the area extraction device.
Figure 17:
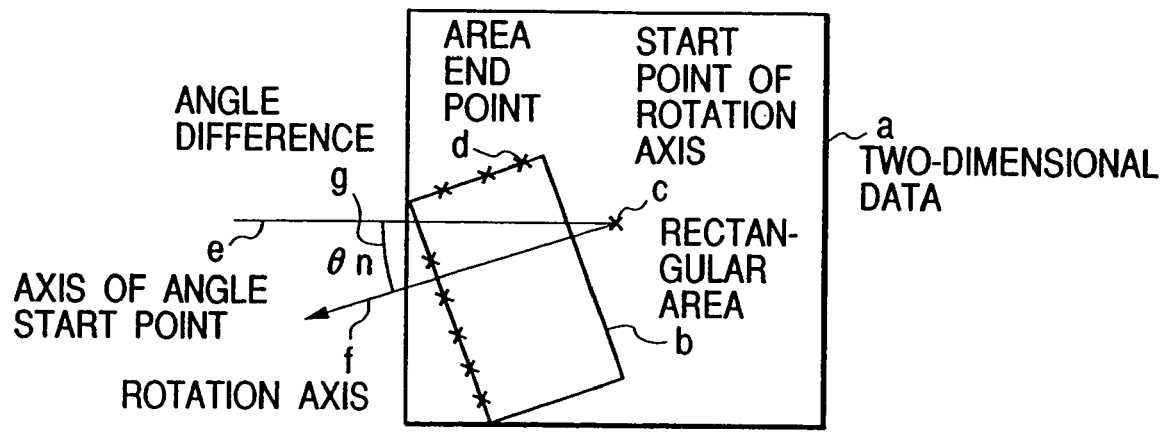
FIG. 17 is a diagram for explaining the processing in the angle extraction device and the area extraction device.

FIG. 16 is a flow chart of a processing sequence in the angle extraction device and the area extraction device in Embodiment 4-1. FIG. 17 is a schematic diagram for explaining the processing in the angle extraction device and area extraction device of the present embodiment, in which "a" represents two-dimensional data (data within a light receiving surface in the case of copiers etc., or data in a sensor surface in the case of X-ray apparatus etc.), "b" a rectangular area (an irradiation area in the case of the X-ray apparatus or a sheet surface in the case of the copiers etc.), "c" a start point of the rotation axis, "d" an area end point, "e" a start axis of angle, "f" a rotation axis, and "g" an angle difference θn between the start axis e of angle and the rotation axis f.

The operation of the present embodiment will be described below according to the flow chart of FIG. 16.

The characteristic quantity calculation means 4101 of FIG. 15 calculates the secondary difference values according to Eq. (51) below (steps S4101 and S4102). In the equation fi(x) represents image data of the i-th row line indicated by the coordinate indication means 4103, SSi(x) the secondary difference values, and "c" a constant.

$$SSi(x)=fi(x-c)-2\times fi(x)+fi(x+c) \tag{51}$$

Then the end point extraction means 4102 extracts a candidate for an end point of the area according to Eq. (52) below (step S4103).

For the left area end of the i-th row, the following equation is used.

$$xi=\min\{SSi(x)|0 \leq x \leq \bar{x}\} \tag{52}$$

In this equation $\bar{x}$ indicates a coordinate on an axis along an indicated direction within the area (the details will be described hereinafter and reference should be made to Eq. (76)). Then the end point memory means 4104 (FIG. 15) stores the coordinate of the area end obtained according to Eq. (52) (step S4104). Then steps S4101 to S4104 are repeated before the processing is complete for all rows indicated by the coordinate indication means 4103 (FIG. 15).

Next, the rotation angle indication means 4105 (FIG. 15) indicates the rotation angle θn (FIG. 17) (step S4105), and the accumulated quantity calculation means 4106 (FIG. 15) performs processing indicated by Eq. (53) to Eq. (57) below to calculate the accumulated quantity L(θn,X) of coordinates x on the aforementioned rotation axis f (FIG. 17) (step S4106). The projection of the area end points onto the aforementioned rotation axis is obtained from projected values of candidate points onto the rotation axis rotated about the start point c(xc,yc) of the aforementioned rotation axis.

$$X_{i\theta n}=-(Xi-xc)*\cos(\theta n)+(Yi-yc)*\sin(\theta n) \tag{53}$$

Here, Xi, Yi represent coordinates of a candidate point for the area end of the i-th row, and $X_{i\theta n}$ represents projected positions of the candidate points for the area ends on the rotation axis x, which are points resulting from rotation by θn about the start point c (FIG. 17) of the aforementioned rotation axis.

$$L(\theta n, x) = \sum_{i=1}^{m} Z(X, X_{i\theta n}) \tag{54}$$

Here, L(θn,X) indicates the number of projected candidate points on the axis resulting from the rotation of the aforementioned rotation axis by θn.

$$\text{Here, } z(X, Xi) = 1, \quad X - d1 \leq Xi \leq X + d1 \tag{55}$$

$$= 0, \quad \text{otherwise,}$$

where d1 is a constant.

Then the accumulated quantity memory means 4107 (FIG. 15) stores the accumulated quantity L(θn,x) obtained by Eq. (54) (step S4107). Further, the processing of steps S4105 to S4107 is repeated for all angles θn indicated by the rotation angle indication means 4105 (FIG. 15).

Then the rotation angle judgment means carries out the processing of Eq. (56) to Eq. (58) below to extract the rotation angle of the area (step S4108).

$$n(\theta n)=L(\theta n, X\max-1)+L(\theta n, X\max)+L(\theta n, X\max+1) \tag{56}$$

This represents the number of overlaps of area ends at the maximum overlap point in the projection of area ends onto the rotation axis. Here, Xmax indicates a coordinate of X that satisfies the following.

$$L(\theta n, X\max)=\max\{L(\theta n, X)|X \in k1\} \tag{57}$$

Here, k1 represents coordinates on the rotation axis.

After all, the rotation angle θ is an angle obtained according to the following equation.

$$\theta=\max\{n(\theta n)|\theta n \in K\} \tag{58}$$

In this equation K is an arbitrary domain of definition.

Then the end point judgment means 4109 (FIG. 15) extracts Xmax satisfying Eq. (59) as a candidate for a left end point of the rectangular area from θ determined by Eq. (58) and the accumulated quantities L(θ,X) stored in the accumulated quantity memory means 4107 (Step S4109).

$$L(\theta, X\max)=\max\{L(\theta, X)|X \in k1\} \tag{59}$$

Likewise, candidates are also extracted for the right, upper, and lower end points. It is, however, noted that they do not always have to be extracted, because the angle of the area is already determined.

As described above, the present embodiment has the following effect because of the use of the secondary difference value; when the area is extracted, boundary points between the area directly irradiated with X-rays and the other areas can be extracted as end points of the area with accuracy even from an object with low X-ray transmittances.

Further, since the angle and end points of the area are determined from the accumulation of end points, the angle and end points of the area can be extracted with accuracy and within short computation time.

In the case of the copiers, FAX, OCR, etc., a necessary area can be extracted based on the area and angle obtained. Further, the present embodiment has the effect of capability of automatically carrying out selection of a sheet with accuracy, because the size of the area can be identified. In addition, even if a sheet is placed obliquely, correction can be made and thus the result is equivalent to that where the sheet is placed at a normal position.

Embodiment 4-2

In the present embodiment, where the image data of a one-dimensional line is f(x) and the secondary difference values thereof are SS(x) defined by Eq. (1), the sign of the primary difference value S(XL) of Eq. (60) below is also added to the operation of extracting the end point XL at the end point extraction means 4102 (FIG. 15).

$$S(XL)=f(XL)-f(XL-d) \tag{60}$$

For example, for extracting the left end point, XL that makes S(XL) negative and that satisfies Eq. (61) below is regarded as a left end point.

$$SS(XL)=\min\{SS(x)|0 \leq x \leq \bar{x}\} \tag{61}$$

As described above, the present embodiment can also take the inclination of the image data outside the area into consideration, because the sign of the primary difference is added to the extraction of the area end. This eliminates erroneous extraction of a quickly changing portion of density in the area and thus the area end point can be extracted with better accuracy.

Embodiment 4-3

In the present embodiment, where the one-dimensional data of the i-th row is fi(x) and is subjected to the filtering process according to Eqs. (64) and (65) below and values resulting from the filtering process are defined as F1i(x) and F2i(x), the characteristic quantity calculation means 4101 (FIG. 15) uses F2i(x) for calculating the secondary difference values defined by Eq. (51).

$$F1i(x) = \min\{fi(x+x1) - h(x1) | -d \leq x1 \leq d\} \quad (64)$$

Further, F2i(x) is defined as follows.

$$F2i(x) = \max\{F1i(x-x1) + h(x1) | -d \leq x1 \leq d\} \quad (65)$$

Here, h(x) is a function defined below.

$$h(x) = 0, \quad -d \leq x1 \leq d \quad (66)$$
$$= \infty, \quad \text{otherwise}$$

Hence, the secondary difference values are calculated as follows.

$$SSi(x) = F2i(x-c) - 2 \times F2i(x) + F2i(x+c) \quad (67)$$

As described above, the present embodiment is arranged to smooth the one-dimensional image data for calculation of the secondary difference values by the filtering process, thereby accomplishing the effect of being not affected by the noise, particularly by the noise on the line.

Embodiment 4-4

Figure 18:
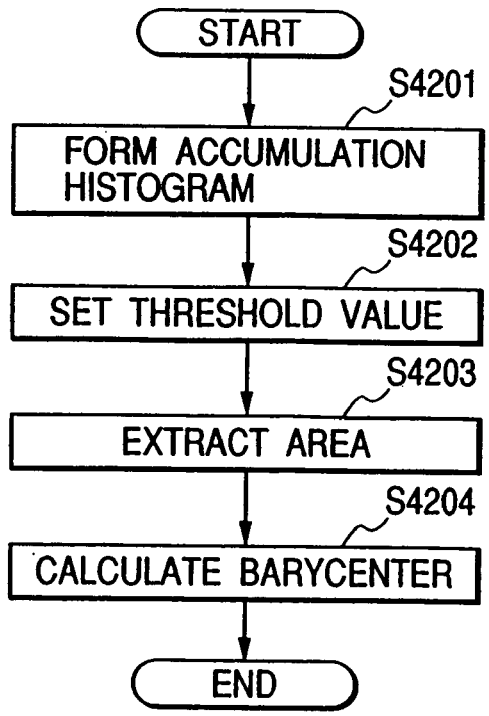
FIG. 18 is a flow chart of a processing procedure sequence for obtaining an approximate center in an area in Embodiment 4-4.

The present embodiment is an example in which the start point c (FIG. 17) of the aforementioned rotation axis is placed at the barycenter of data not less than a fixed density. The flow of processing will be described according to a flow chart of a procedure sequence for obtaining an approximate center in the area, shown in FIG. 18.

First, an accumulation histogram of whole image data is produced in step S4201 and upper densities above TH % are extracted (steps S4202, S4203, S4204). Then the barycenter of the upper densities above TH % is regarded as an approximate barycenter of the rectangular area.

$$\bar{x} = \frac{\iint f(x,y) x \, dx \, dy}{\iint f(x,y) \, dx \, dy} \quad (68)$$

$$\bar{y} = \frac{\iint f(x,y) y \, dx \, dy}{\iint f(x,y) \, dx \, dy} \quad (69)$$

Here, f(x,y) represents an image of the upper densities above TH % and $\bar{y}$, $\bar{x}$ stand for the barycenter.

As described above, since the present embodiment is arranged to calculate the barycenter of data above the fixed density value, the present embodiment can extract the approximate barycenter of the area of interest with accuracy without being affected by the peripheral data, even if the object area is in the peripheral part of the two-dimensional image data.

Further, since the start point c (FIG. 17) of the aforementioned rotation axis f is placed in the object area, degrees of change in accumulated quantities of area ends become large against rotation of the rotation axis and the present embodiment can thus enjoy the effect of capability of extracting the rotation angle and area with better accuracy.

Embodiment 4-5

The present embodiment is arranged as follows. When the end point extraction means 4102 (FIG. 15) extracts an end point, a point is not extracted as a candidate for an end point if f maxi<Th at the point, f maxi being defined below.

$$f \max i = \max\{fi(x) | x \in k\} \quad (70)$$

Here, "k" indicates a domain of definition of row data and Th a fixed threshold value.

As described above, the present embodiment can eliminate end points that can be points outside the object area with high possibilities and thus can extract the area and the angle of the area with better accuracy.

Embodiment 4-6

The present embodiment uses a first order differential or a higher order differential as a characteristic quantity at the characteristic quantity calculation means 4101 (FIG. 15). When Di(x) represents differential values of the i-th row, the end point extraction means 4102 (FIG. 15) extracts a point satisfying the condition of xi≧th as a candidate for an end point on the occasion of extracting a candidate for the left end point of the i-th row.

As described above, the present embodiment has the effect of shorter computation time, because it adopts the simple differentiation.

Embodiment 4-7

Figure 19:
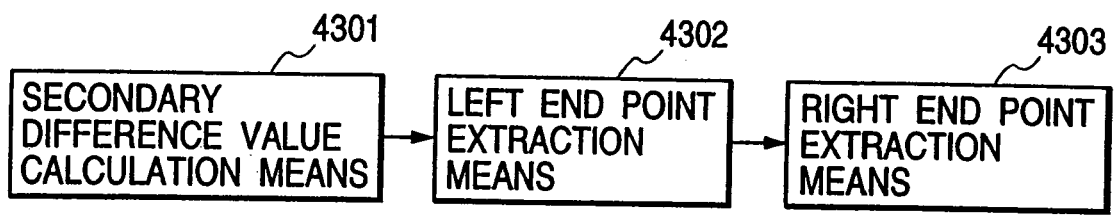
FIG. 19 is a block diagram to show the structure of an area extraction device in Embodiment 4-7.
Figure 20:
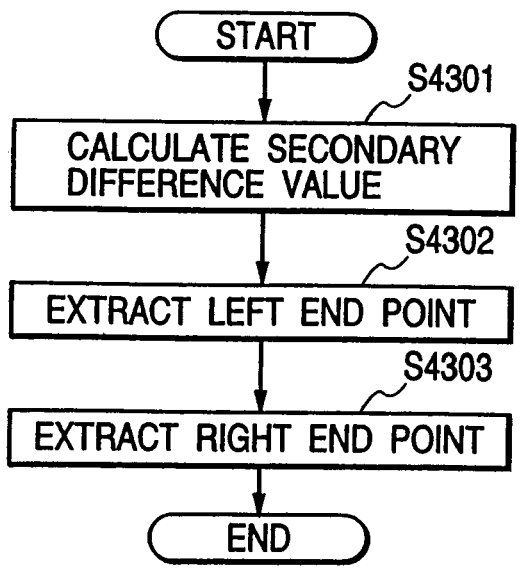
FIG. 20 is a flow chart of a processing procedure sequence in the area extraction device of Embodiment 4-7.

FIG. 19 is a block diagram to show the structure of an area extraction device according to the present embodiment. In FIG. 19, reference numeral 4301 designates a secondary difference value calculation means for calculating the secondary difference values of one-dimensional image data in a designated direction (for example, which is determined according to the value determined by the angle extraction device described above), 4302 a left end point extraction means for extracting a left end point of the area, based on the secondary difference values calculated at the secondary difference value calculation means 4301, and 4303 a right end point extraction means for extracting a right end point of the area, based on the secondary difference values calculated at the secondary difference value calculation means 4301. FIG. 20 is a flow chart of a processing procedure sequence in the area extraction device according to the present embodiment.

The flow of the processing in the present embodiment will be described according to FIG. 20. The secondary difference value calculation means 4301 (FIG. 19) calculates the secondary difference values SS(x) according to a calculation equation defined by Eq. (71) below (step S4301). Here, f(x) represents the one-dimensional data of a line crossing the area in the designated direction and x represents coordinates thereof. Further, "d" denotes a constant indicating a difference distance.

$$SS(d)=f(x-d)-2\times f(x)+f(x+d) \tag{71}$$

The left end point extraction means 4302 (FIG. 19) extracts the left end point x1 according to Eq. (72) below (step S4302). Here, $\bar{x}$ represents a coordinate on the horizontal axis in the area.

$$SS(x1)=\min\{SS(x)|0 \leq x \leq \bar{x}\} \tag{72}$$

Then the right end point extraction means 4203 (FIG. 19) extracts the right end point x2 according to Eq. (73) below (step S4303).

$$SS(x2)=\min\{SS(x)|\bar{x} \leq x \leq \text{Length}\} \tag{73}$$

Here, "Length" indicates the length of the image data along the horizontal axis.

As described above, since the present embodiment uses the secondary difference values, it has the effect of capability of extracting the area with accuracy even if the density change is gentle at the area end.

Embodiment 4-8

The present embodiment uses the projection of the image area as defined by Eq. (74) below, as the one-dimensional data f(x) in aforementioned Eq. (71).

$$f(x) = \int_b^c f(x, y) \, dy \tag{74}$$

Here, f(x,y) represents the image data in the designated direction and x, y coordinates on the horizontal and vertical axes, respectively (which are inclined in a certain direction). Further, "b", "c" represent an arbitrary domain across the object area.

As described above, since the present embodiment uses the projection in the image area, it has the same effect as in the case of averaging the data of the image area. Therefore, the present embodiment can prevent the extraction from being affected by the noise inside and outside the object area and thus can extract the area with better accuracy.

Embodiment 4-9

Figure 21:
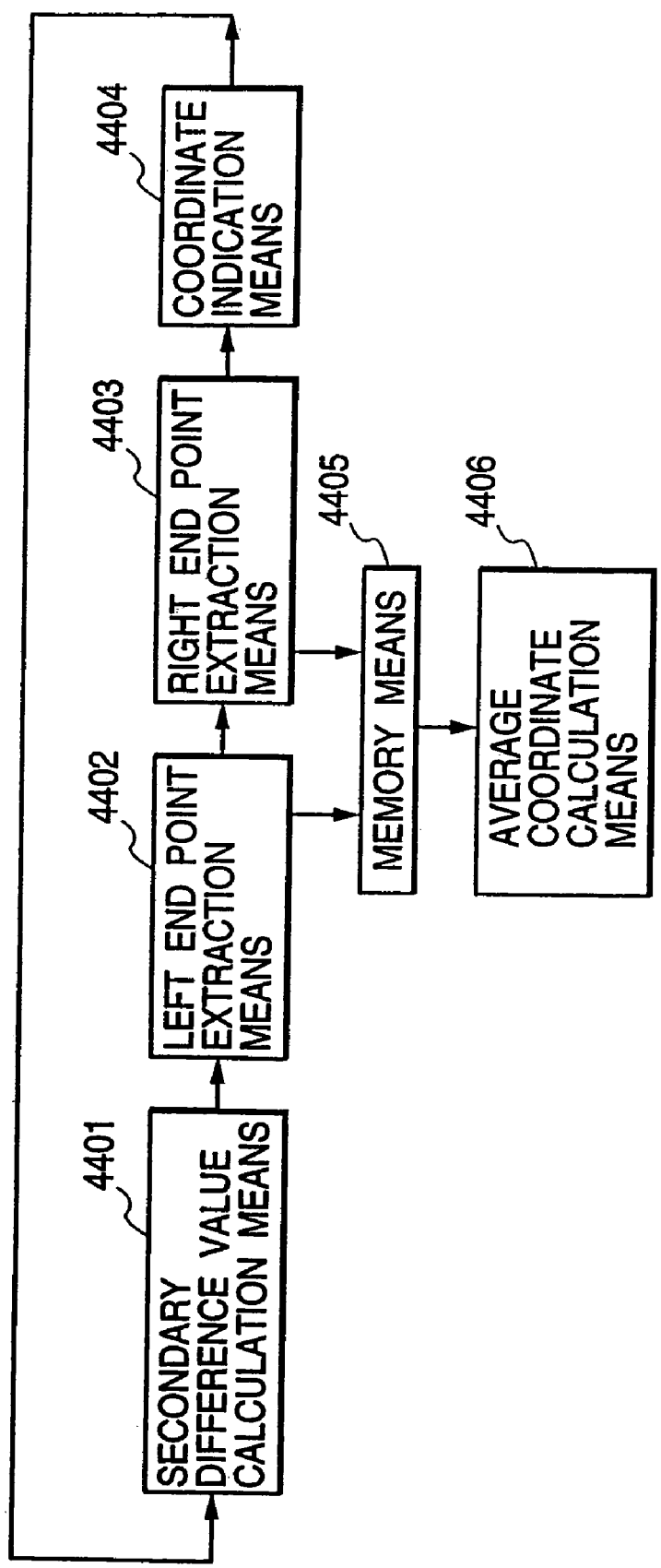
FIG. 21 is a block diagram to show the structure of an area extraction device in Embodiment 4-9.

FIG. 21 is a block diagram to show the structure of an area extraction device according to the present embodiment. In FIG. 21, reference numeral 4401 designates a secondary difference value calculation means for calculating the secondary difference values of one-dimensional image data in a designated direction (for example, which is determined according to the value determined by the angle extraction device described above) indicated by a coordinate indication means 4404, 4402 a left end point extraction means for extracting a left end point of the area, based on the secondary difference values calculated at the secondary difference value calculation means 4401, a right end point extraction means for extracting a right end point of the area, based on the secondary difference values calculated at the secondary difference value calculation means 4401, and 4404 the coordinate indication means for indicating a coordinate of one-dimensional data for calculation of the secondary difference values at the secondary difference value calculation means 4401 after extraction of the right area end at the right end point extraction means 4403.

Numeral 4405 denotes a memory means for storing coordinates of right end points and left end points extracted at the left end point extraction means 4402 and at the right end point extraction means 4403, and 4406 an average coordinate calculation means for calculating an average coordinate for each end point from the left and right ends stored in the memory means 4405.

Figure 22:
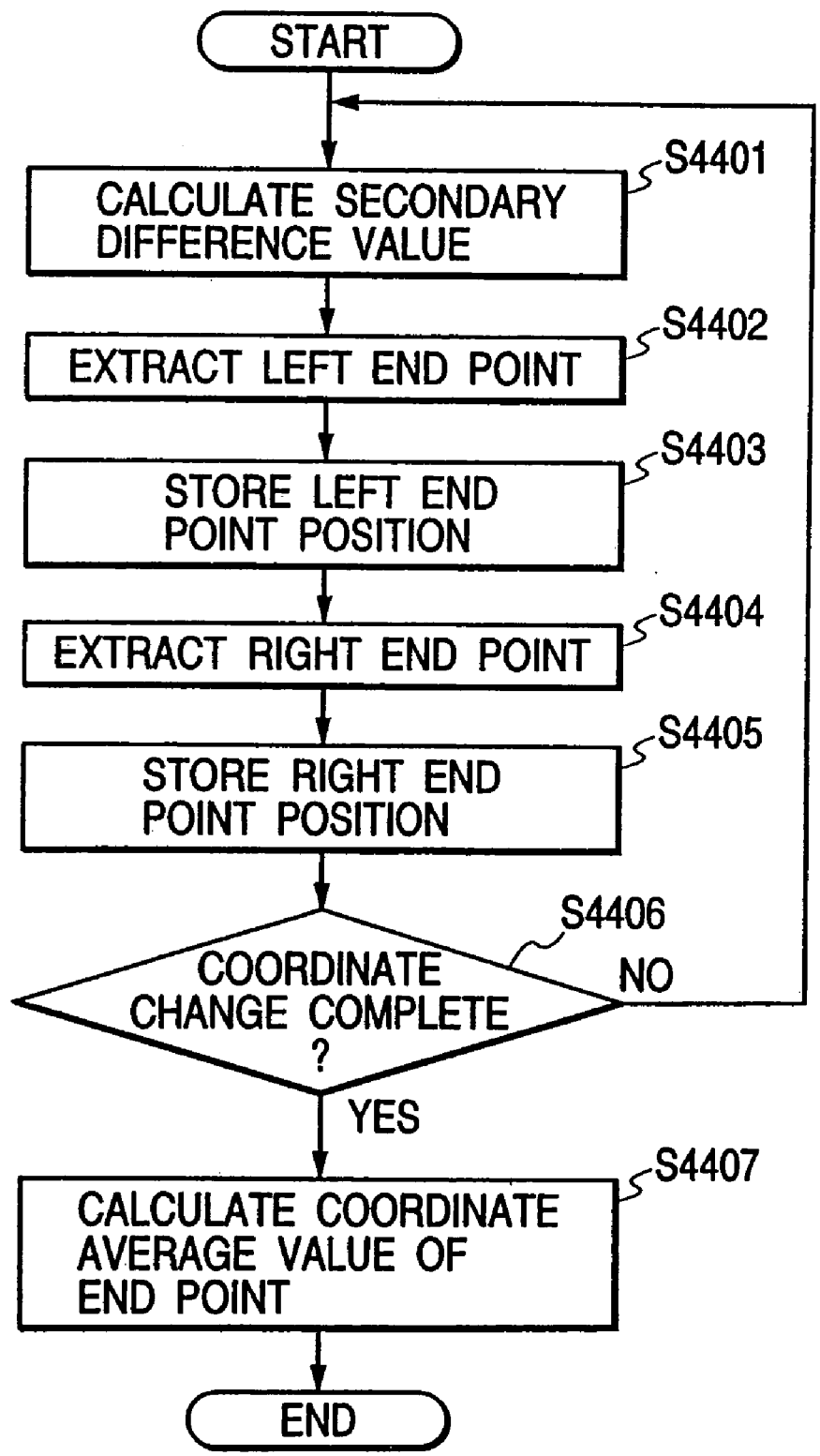
FIG. 22 is a flow chart of a processing procedure sequence in the area extraction device of Embodiment 4-9.

FIG. 22 is a flow chart of a processing procedure sequence of the area extraction device according to the present embodiment. The operation will be described according to FIG. 22.

The secondary difference value calculation means 4401 (FIG. 21) calculates the secondary difference values SSi(x) according to a calculation equation defined by Eq. (75) below (step S4401). Here, fi(x) represents one-dimensional data of a line crossing the area in the designated direction, x coordinates thereof, and "i" a coordinate of the row in the designated direction indicated by the coordinate indication means 4404. Here, "d" represents a constant indicating a difference distance.

$$SSi(x)=fi(x-d)-2\times fi(x)+fi(x+d) \tag{75}$$

Then the left end point extraction means 4402 (FIG. 21) extracts the left area end XLi according to Eq. (76) below (step S4402).

Here, $\bar{x}$ represents a coordinate on the axis along the designated direction in the area.

$$SSi(XLi)=\min\{SSi(x)|0 \leq x \leq \bar{x}\} \tag{76}$$

Then the memory means 4405 (FIG. 21) stores the left area end XLi extracted at the left end point extraction means 4402 (step S4403).

Next, the right end point extraction means (FIG. 21) extracts the right area end XRi according to Eq. (77) below (step S4404).

$$SSi(XRi)=\min\{SSi(x)|\bar{x} \leq x \leq \text{Length}\} \tag{77}$$

Here, "Length" represents the length of the image data along the horizontal axis in the predetermined direction.

Then the memory means 4405 (FIG. 21) stores the right area end XRi extracted at the right end point extraction means 4403 (step S4404).

Next, the coordinate indication means 4404 (FIG. 21) indicates a coordinate of a row in a new designated direction and step S4401 to step S4405 are repeated. An indication of the end of the loop is issued from the coordinate indication means 4404 (FIG. 21) (step S4406).

Next, after completion of the above extraction of the left and right end points, the average coordinate calculation means 4406 (FIG. 21) calculates an average of the coordinates of the left and right end points stored in the memory means 4405 (step S4407).

As described above, since the present embodiment uses the secondary difference values, the boundary points of the area can be extracted with accuracy even if the density values vary gently at the boundary of the area.

Further, since the area end is determined from the average of the area ends on plural lines, the present embodiment has the effects of being more resistant to the noise and capable of extracting the area with higher accuracy than in the case using a single point.

Embodiment 4-10

In the present embodiment, where the image data of a one-dimensional line in the designated direction is expressed by f(x) and the secondary difference values thereof by SS(x) defined by Eq. (78) below, the sign of the primary difference value S(XL) defined by Eq. (79) below is added to the extraction of the left end point XL at the left end point extraction means 4302 (FIG. 19) or 4402 (FIG. 21).

$$SS(x)=f(x-d)-2\times f(x)+f(x+d) \quad (78)$$

$$S(XL)=f(XL)-f(XL-d) \quad (79)$$

For example, for extracting a left end point, XL that makes s(XL) negative and that satisfies Eq. (80) below is regarded as a left end point.

$$SS(XL)=\min\{SS(x)|0\leq x\leq \bar{x}\} \quad (80)$$

$$S(XR)=f(XR+d)-f(XR) \quad (81)$$

Likewise, where the right end point is extracted at the right end point extraction means 4303 (FIG. 19) or 4403 (FIG. 21), XR that makes S(XR) defined by above Eq. (81) negative and that satisfies Eq. (82) below is regarded as a right area end.

$$SS(XR)=\min\{SS(x)|\bar{x}\leq x\leq \text{Length}\} \quad (82)$$

As described above, since the present embodiment is arranged to add the sign of the primary difference to the extraction of the area end, it can also take the inclination of the image data outside the area into consideration. Therefore, erroneous extraction can be prevented at a quickly changing portion of density in the area, so that the area can be extracted with better accuracy.

Embodiment 4-11

In the present embodiment, where the one-dimensional data in the designated direction is defined by f(x) and values resulting from the filtering process according to Eqs. (83), (84) below are defined by F1(x), F2(x), the values F2(x) are used for calculation of the secondary difference values at the secondary difference value calculation means 4301 (FIG. 19) or 4401 (FIG. 21).

$$F1(x)=\min\{f(x+x1)-h(x1)|-d\leq x1\leq d\} \quad (83)$$

Further, F2(x) is defined as follows.

$$F2(x)=\max\{F1(x-x1)+h(x1)|-d\leq x1\leq d\} \quad (84)$$

Here, h(x) is a function defined as follows.

$$h(x) = 0, \quad -d \leq x1 \leq d \quad (85)$$
$$= -\infty, \quad \text{otherwise}$$

As described above, since the present embodiment is arranged to smooth the one-dimensional image data for the computation of the secondary difference values by the filtering process, it has the effect of being not affected by the noise, particularly, by the noise on the line.

While the present invention has been described with respect to what is presently considered to be the preferred embodiments, it is to be understood that the invention is not limited to the disclosed embodiments. To the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. An image processing apparatus comprising:
    image input means for inputting to the image processing apparatus an image data which is obtained in a case that an irradiation diaphragm is used or in a case that the irradiation diaphragm is not used;
    detecting means for calculating candidates for edge points of an irradiation area from the image area;
    evaluating means for calculating an evaluation value for evaluating positional relations among coordinates of the candidates for the edge points of the irradiation area calculated by said detecting means; and
    judging means for judging whether the input image is obtained by the use of the irradiation diaphragm or not, based on the evaluation value calculated by said evaluating means,
    wherein the evaluation value corresponds to an approximation of the edge points, and the judging means judges that the irradiation diaphragm is used at the time of obtaining the image data in a case that the evaluation value exceeds the predetermined value.

2. An image processing apparatus according to claim 1, wherein the detecting means comprises calculating means for calculating a secondary difference value for a plurality of lines in the image data, and means for obtaining candidates for the edge points for respective lines.

* * * * *